US012580060B2

(12) United States Patent
Siegel

(10) Patent No.: US 12,580,060 B2
(45) Date of Patent: *Mar. 17, 2026

(54) SYSTEMS AND METHODS FOR PRESCRIPTION MANAGEMENT

(71) Applicant: PERKSRX, LLC, New York, NY (US)

(72) Inventor: Robert Max Siegel, New York, NY (US)

(73) Assignee: PERKSRX, LLC, Fort Mill, SC (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/828,594

(22) Filed: Sep. 9, 2024

(65) Prior Publication Data

US 2024/0428916 A1      Dec. 26, 2024

Related U.S. Application Data

(63) Continuation of application No. 18/295,279, filed on Apr. 4, 2023, now Pat. No. 12,119,098, which is a
(Continued)

(51) Int. Cl.
*G16H 20/10*          (2018.01)
*G06Q 30/00*          (2023.01)
(Continued)

(52) U.S. Cl.
CPC ......... *G16H 20/10* (2018.01); *G06Q 30/0283* (2013.01); *G06Q 30/0613* (2013.01); *G06Q 30/0639* (2013.01); *G16H 40/63* (2018.01)

(58) Field of Classification Search
CPC .... G16H 20/10; G16H 40/63; G06Q 30/0283; G06Q 30/0613; G06Q 30/0639
See application file for complete search history.

(56) References Cited

U.S. PATENT DOCUMENTS 8,712,797 B1      4/2014   Bezdek et al.
2004/0225527 A1*  11/2004  Holz ..................... G16H 40/63
                                                          705/2
(Continued)

FOREIGN PATENT DOCUMENTS

KR          20210025819 A        3/2021

OTHER PUBLICATIONS

O. Rajabi Shishvan, D.-S. Zois and T. Soyata, "Machine Intelligence in Healthcare and Medical Cyber Physical Systems: A Survey," in IEEE Access, vol. 6, pp. 46419-46494, 2018, doi: 10.1109/ACCESS.2018.2866049. (Year: 2018) (Year: 2018) (Year: 2018).*

(Continued)

*Primary Examiner* — Sun M Li
(74) *Attorney, Agent, or Firm* — Potomac Law Group, PLLC; Jamaica Szeliga

(57)                    ABSTRACT

Systems and methods are disclosed for interacting with a prescription submission system, a cloud computing system, and a prescription processing system to transmit prescriptions to an optimal pharmacy based on user information. User information, a location, and a prescription including a treatment e.g., medicine) may be received from a user or a health care professional. A plurality of pharmacies may be identified based at least on availability of the treatment, each of the plurality of pharmacies meeting a location criterion based on the location. Treatment pricing may be identified for each of the identified plurality of pharmacies. The plurality of pharmacies and the corresponding pricing information may be transmitted to a computing device. A selected pharmacy from the plurality of pharmacies may be received, from the computing device, and, the prescription may be transmitted to be received at the selected pharmacy's prescription processing system.

20 Claims, 9 Drawing Sheets

100

RECEIVE USER INFORMATION
102

RECEIVE A LOCATION
104

RECEIVE A PRESCRIPTION ASSOCIATED WITH THE USER INFORMATION, THE PRESCRIPTION INCLUDING A TREATMENT
106

IDENTIFY A PLURALITY OF PHARMACIES BASED ON AVAILABILITY OF THE TREATMENT AND A LOCATION CRITERION
108

IDENTIFY TREATMENT PRICING INFORMATION FOR EACH OF THE PLURALITY OF PHARMACIES
110

TRANSMIT THE PLURALITY OF PHARMACIES AND CORRESPONDING PRICING INFORMATION
112

RECEIVE A SELECTED PHARMACY
114

TRANSMIT THE PRESCRIPTION TO THE SELECTED PHARMACY
118

Related U.S. Application Data continuation of application No. 17/011,222, filed on Sep. 3, 2020, now Pat. No. 11,651,843.

(60) Provisional application No. 62/895,642, filed on Sep. 4, 2019.

(51) Int. Cl.
G06Q 30/0283 (2023.01)
G06Q 30/0601 (2023.01)
G16H 40/63 (2018.01)

(56) References Cited

U.S. PATENT DOCUMENTS

| | | | | |
|---|---|---|---|---|
| 2007/0143137 | A1* | 6/2007 | Ross | G16H 20/10 |
| | | | | 600/300 |
| 2007/0250341 | A1* | 10/2007 | Howe | G06Q 10/10 |
| | | | | 600/300 |
| 2012/0004929 | A1* | 1/2012 | Nadas | G16H 20/10 |
| | | | | 705/2 |
| 2012/0253831 | A1 | 10/2012 | John et al. | |
| 2014/0180705 | A1* | 6/2014 | Stueckemann | G16H 20/10 |
| | | | | 705/2 |
| 2014/0278520 | A1 | 9/2014 | Abuzeni | |
| 2015/0142479 | A1* | 5/2015 | Porter | G06Q 40/08 |
| | | | | 705/4 |
| 2016/0034668 | A1* | 2/2016 | Rourke | G16H 10/60 |
| | | | | 705/2 |
| 2016/0358294 | A1 | 12/2016 | Berger et al. | |
| 2017/0308981 | A1* | 10/2017 | Razavian | G16H 40/60 |

OTHER PUBLICATIONS

A Secure Intelligent Decision Support System for Prescribing Medication, by Adebayo Omotosho, Emuoyibofarhe Justice, [Submitted on Mar. 27, 2015], Computers and Society (cs.CY), arXiv:1503.08158 [cs.CY], for this version), https://doi.org/10.48550/arXiv.1503.08158 (Year 2015). (Year: 2015) (Year: 2015).*

A Secure Intelligent Decision Support System for Prescribing Medication, by Adebayo Omotosho, Emuoyibofarhe Justice, [Submitted on Mar. 27, 2015], Computers and Society (cs.CY), arXiv:1503.08158 [cs.CY], (or arXiv:1503.08158v1 [cs.CY] for this version), https://doi .org/10.48550/arXiv.1503.08158 (Year: 2015).

F. Fruggiero, R. Iannone, G. Martino, S. Miranda and S. Riemma, "A forecast model for pharmaceutical requirements based on an artificial neural network," Proceedings of 2012 IEEE International Conference on Service Operations, 2012, pp. 263-268, doi: 10.1109/SOLI.2012.627 (Year: 2012).

GETMYRX, GETMYRXFAQ, Logo, 2014, (6 pages).

H. Y. Putra and M. L. Khodra, "Descriptive And Predictive Analysis Of Mail Order Pharmacy," 2018 International Workshop on Big Data and Information Security (IWBIS), Jakarta, Indonesia, 2018, pp. 31-36, doi: 10.1109/IWBIS.2018.8471714. (Year: 2018).

Lumpkin, Daniel, Medisafe: A Prescription Medication App That Could Actually Change the World, Tech Features App., Jan. 15, 2016 (3 pages).

Medimpact Healthcare Systems Inc., Medimpact2Go FAQ, pbm.medimpact.com, 2018, (6 pages).

Mitroff, Sarah, Why I Ditched Walgreens for This Pharmacy App, CNet, May 9, 2019, (5 pages).

O. Rajabi Shishvan, D.-S. Zois and T. Soyata, "Machine Intelligence in Healthcare and Medical Cyber Physical Systems: A Survey," in IEEE Access, vol. 6, pp. 46419-46494, 2018, doi: 10.1109/ACCESS.2018.2866049. (Year: 2018).

Omotosho .A. & Emuoyibofarhe .O.J (2012). A Secure Intelligent Decision Support System for Prescribing Medication. Computing, Information Systems & Development Informatics Journal. vol 3, No. 3. pp 9-18. Available online at www.cisdijournal.net (Year: 2012).

Perez MM, Gonzalez GV, Dafonte C. The Development of an RFID Solution to Facilitate the Traceability of Patient and Pharmaceutical Data. Sensors (Basel). 2017;17(10):2247. Published Sep. 29, 2017. doi:10.3390/s17102247 (Year: 2017).

Pharmacy Times, Rapid Drug Delivery: Where is the Uber for Pharmacy?, pharmacytimes.com, vol. 85, No. 6, Jun. 7, 2015 (3 pages).

Pill Pack, Pill Pack Service Guide, Amazon, 2018, (21 pages).

Resources News, NowRx Reinvents Pharmacy Model With One-Hour On-Demand Delivery of Prescription Medication to Consumers, Dow Jones, Jun. 14, 2017 (1 page).

RxSaver by Retailmenot, RxSaver Mobile Apps, (6 pages).

St. Denis, Demian, et al., Nimble Usability Evaluation, 2019 (62 pages).

Y.-Y. Ou, S.-P. Tseng, J. Lin, X.-P. Zhou, J.-F. Wang and T.-W. Kuan, "Automatic Prescription Recognition System," 2018 International Conference on Orange Technologies (ICOT), 2018, pp. 1-4, doi: 10.1109/ICOT.2018.8705828. (Year: 2018).

D. Habamwabo and B. A. Mpagazi. "Drug Accessibility and Availability Tool: Case of Rwanda," 2017 IEEE International Conference on Bioinformatics and Biomedicine (BIBM), 2017, pp. 1571-1575, doi: 10.1109/BIBM.2017.8217894. (Year: 2017).

Yanjiang Yang et al. "A Smart-card Enabled Privacy Preserving E-Prescription System," in IEEE Transactions on Information Technology in Biomedicine, vol. 8, No. 1, pp. 47-58, Mar. 2004, doi: 10.1109/TITB.2004.824731. (Year: 2004).

* cited by examiner

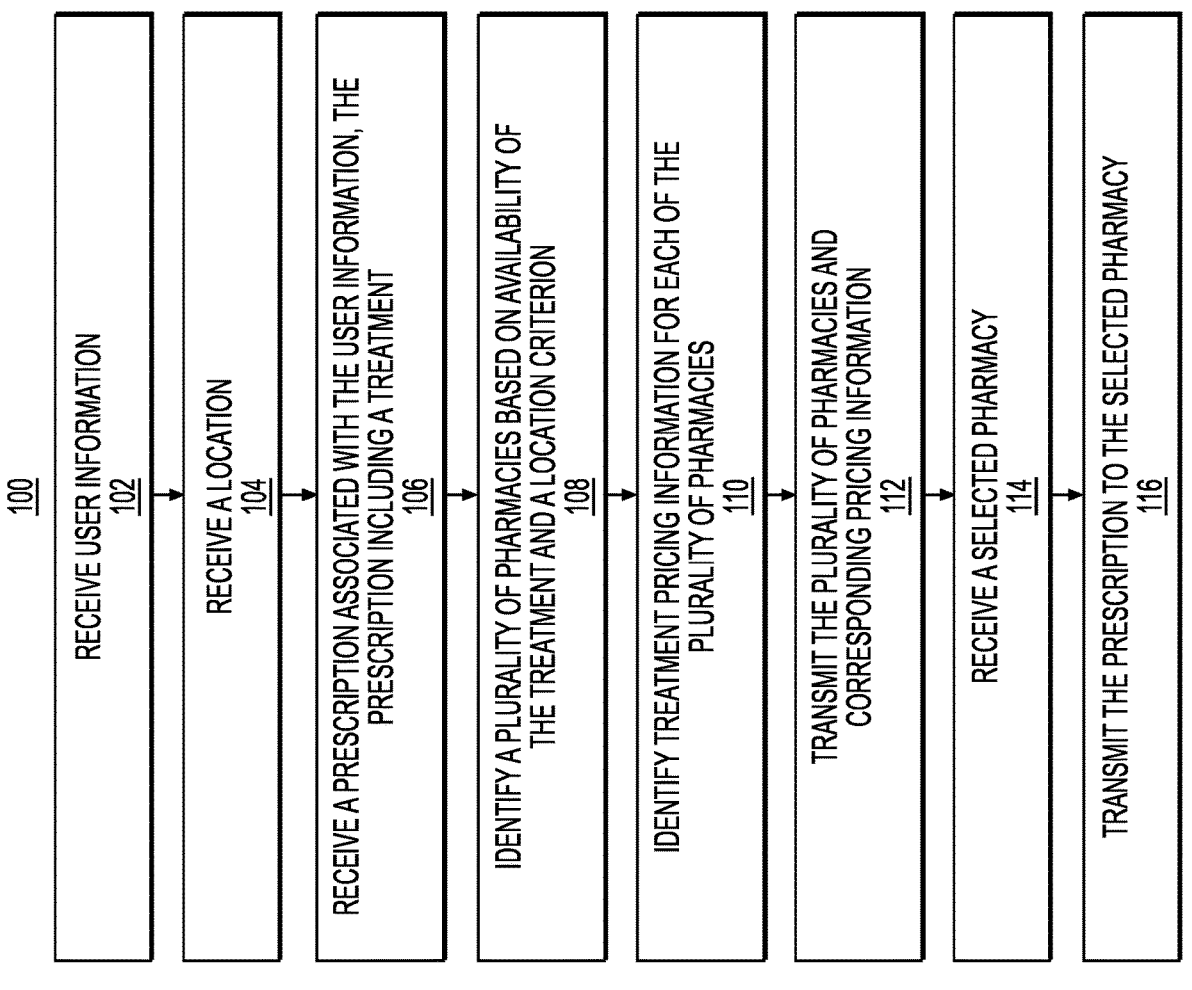

100

RECEIVE USER INFORMATION
102

RECEIVE A LOCATION
104

RECEIVE A PRESCRIPTION ASSOCIATED WITH THE USER INFORMATION, THE PRESCRIPTION INCLUDING A TREATMENT
106

IDENTIFY A PLURALITY OF PHARMACIES BASED ON AVAILABILITY OF THE TREATMENT AND A LOCATION CRITERION
108

IDENTIFY TREATMENT PRICING INFORMATION FOR EACH OF THE PLURALITY OF PHARMACIES
110

TRANSMIT THE PLURALITY OF PHARMACIES AND CORRESPONDING PRICING INFORMATION
112

RECEIVE A SELECTED PHARMACY
114

TRANSMIT THE PRESCRIPTION TO THE SELECTED PHARMACY
116

| PHARMACY | DISTANCE | PRICE |
|---|---|---|
| PHARMACY A | 3 mi | $50 |
| PHARMACY B | 1.2 mi | $52 |
| PHARMACY C | 4 mi | $55 |
| PHARMACY D | 2.3 mi | $67 |
| PHARMACY E | 5 mi | $68 |
| PHARMACY F | .2 mi | $74 |
| PHARMACY G | 1 mi | $98 |
| PHARMACY H | 4.4 mi | $105 |

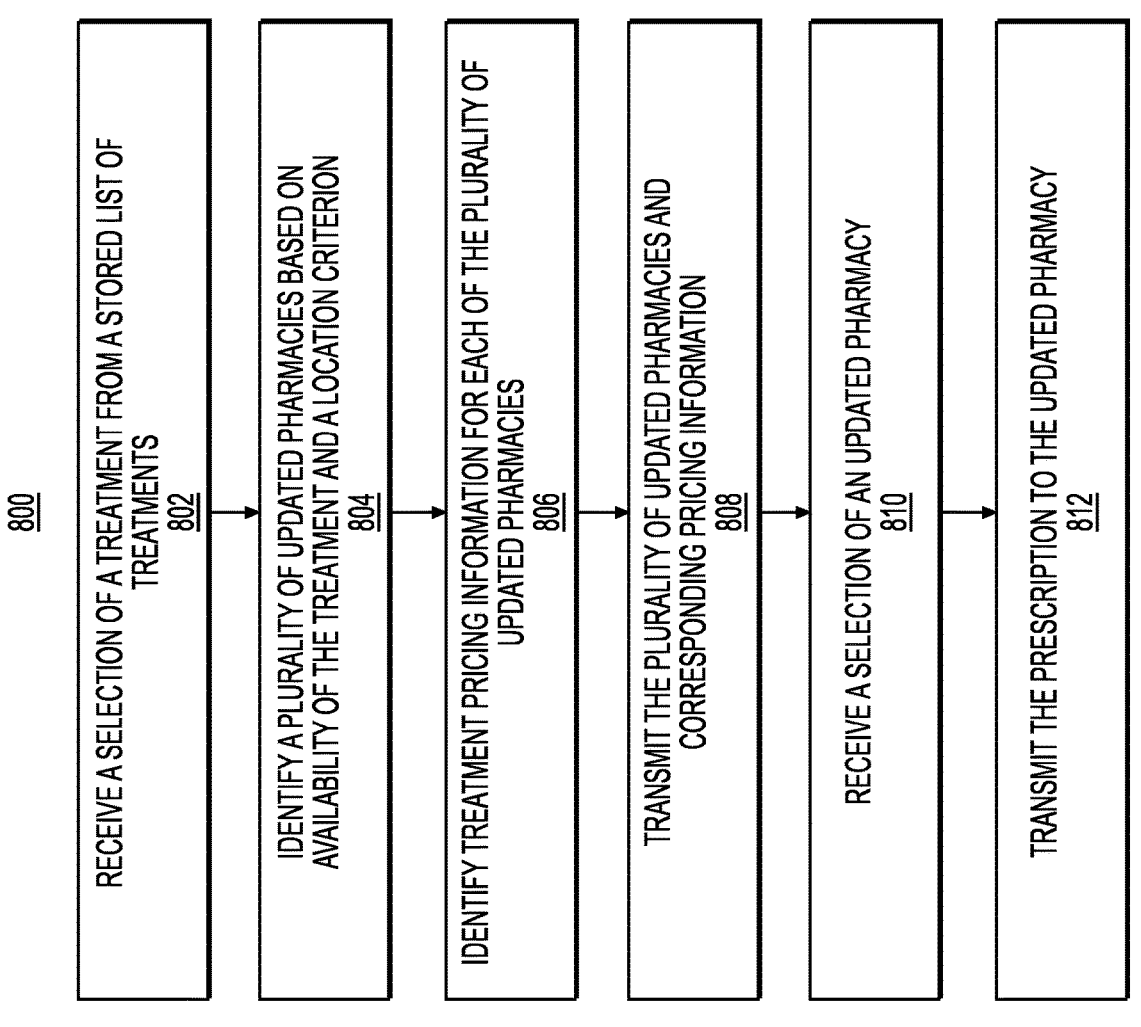

800

RECEIVE A SELECTION OF A TREATMENT FROM A STORED LIST OF TREATMENTS
802

IDENTIFY A PLURALITY OF UPDATED PHARMACIES BASED ON AVAILABILITY OF THE TREATMENT AND A LOCATION CRITERION
804

IDENTIFY TREATMENT PRICING INFORMATION FOR EACH OF THE PLURALITY OF UPDATED PHARMACIES
806

TRANSMIT THE PLURALITY OF UPDATED PHARMACIES AND CORRESPONDING PRICING INFORMATION
808

RECEIVE A SELECTION OF AN UPDATED PHARMACY
810

TRANSMIT THE PRESCRIPTION TO THE UPDATED PHARMACY
812

FIG. 8

SYSTEMS AND METHODS FOR PRESCRIPTION MANAGEMENT

CROSS-REFERENCE TO RELATED APPLICATION

This application is a continuation of U.S. application Ser. No. 18/295,279, filed on Apr. 4, 2023, which is a continuation of U.S. patent application Ser. No. 17/011,222, filed on Sep. 3, 2020, which claims the benefit of priority from U.S. Provisional Application No. 62/895,642, filed on Sep. 4, 2019, each of which is incorporated by reference herein in its entirety.

TECHNICAL FIELD

The present disclosure relates to systems and methods for prescription management. More particularly, the present disclosure relates to systems and methods for using one or more processors to optimize pharmacy selection for medical treatments, based on a prescription and on user information.

BACKGROUND

Drugstores, healthcare centers, retail stores, doctor's offices, hospitals, and grocery stores, are some locations with pharmacies where patients can obtain prescribed treatments such as prescription drugs, drug-related products, and therapies. While the number of pharmacy locations increases, fulfilling and organizing prescriptions has remained sub-optimal. Notably, patients rely on healthcare professionals and other third-parties to manage their prescriptions, which often results in reduced focus on the patient's needs.

Currently, during a medical visit, such as a doctor's appointment or hospital stay, patients are either handed a prescription on a pad or are asked to pick a pharmacy to which the healthcare professional can submit an electronic prescription. The patient must quickly, and sometimes arbitrarily, pick a pharmacy without having the opportunity to consider various factors such as convenience, location, or price. After the patient chooses a pharmacy, the healthcare professional submits the prescription, usually through a system, which is automatically dispatched to the selected pharmacy.

Under this current system, patients cannot easily control, manage, view, and/or change the pharmacy and/or the use of their own prescription.

The background description provided herein is for the purpose of generally presenting the context of the disclosure. Unless otherwise indicated herein, the materials described in this section are not prior art to the claims in this application and are not admitted to be prior art, or suggestions of the prior art, by inclusion in this section.

SUMMARY OF THE DISCLOSURE

One embodiment provides systems and methods of interacting with a prescription submission system, a cloud computing system, and a prescription processing system to transmit prescriptions to an optimal pharmacy based on user information. A computer-implemented method and system for prescription management includes receiving user information at one or more processors, receiving a location at the one or more processors, and receiving a prescription associated with the user information at the one or more processors, the prescription comprising a treatment (e.g., a medicine, a therapy, a device, an application, an object, etc.). The prescription may be provided by one of a user and a health care professional. The method and system further includes identifying, via the one or more processors, a plurality of pharmacies based at least on availability of the treatment, each of the plurality of pharmacies meeting a location criterion (e.g., selected from one of a distance proximity, a minimum number of pharmacies, etc.) based on the location, identifying treatment pricing information for each of the identified plurality of pharmacies, and transmitting, via the one or more processors, the plurality of pharmacies and the corresponding pricing information for each of the plurality of pharmacies, to a computing device. The method and system further includes receiving, at a first time and via the one or more processors, a selected pharmacy from the plurality of pharmacies, from the computing device, and, transmitting, via the one or more processors, the prescription to be received at the selected pharmacy's prescription processing system.

The method and system further includes receiving, at a second time subsequent to the first time and via the one or more processors, an updated pharmacy, from the computing device and transmitting, via the one or more processors, the prescription to the updated pharmacy's prescription processing system.

The user information may be provided by a computing device, may be transmitted by the computing device to the one or more processors, and may include one or more of an insurance information, a time preference information, a discount information, rewards information, or review preference information.

Additionally, the method and system includes determining one or more alternative treatments corresponding to the treatment and identifying the plurality of pharmacies further based on the one or more alternative treatments.

Identifying pricing information may include adjusting a base treatment pricing based on the user information. Identifying the pricing information may include adjusting the base treatment pricing based on the insurance information.

Identifying the plurality of pharmacies may further include using a trained machine learning model, wherein the inputs to the trained machine learning model include the user information, the location, and the prescription.

Transmitting the plurality of pharmacies and the corresponding pricing information may include a format that visually shows the plurality of pharmacies and the corresponding pricing information on a map.

Another embodiment provides a computer-implemented method and system for prescription including receiving user information at one or more processors, receiving a location at the one or more processors, receiving a prescription associated with the user information at the one or more processors, the prescription comprising a treatment, and identifying an alternative treatment based on the treatment. The method and system further includes identifying, via the one or more processors, a plurality of pharmacies based on at least one of an availability of the treatment and an availability of the alternative treatment, each of the plurality of pharmacies meeting a location criterion based on the location, identifying pricing information of at least one of the treatment and the alternative treatment, for each of the identified plurality of pharmacies, and transmitting, via the one or more processors, the plurality of pharmacies and the corresponding pricing information for each of the plurality of pharmacies, to a computing device. The alternative treatment may be one of a generic treatment, an alternative therapy, or a medical device. Identifying pricing information of at least one of the treatment and the alternative treatment may further include identifying the lower of the pricing information of the treatment and the pricing information of the alternative treatment. The alternative treatment may be determined based on a database configured to provide alternative treatment information.

Another embodiment provides a system including a computing device, including at least one processor, a cloud electronic system, including at least one processor, and a selected pharmacy prescription processing system, including at least one processor. The computing device may be configured to provide user information, a prescription associated with the user information and comprising a treatment, and a location. The cloud electronic system may be configured to receive the user information, receive the location, receive the prescription associated with the user information, identify a plurality of pharmacies, based at least on availability of the treatment, each of the plurality of pharmacies meeting a location criterion based on the location, identify treatment pricing information for each of the identified plurality of pharmacies, transmit the plurality of pharmacies and the corresponding pricing information for each of the plurality of pharmacies, to the computing device, receive a selected pharmacy from the plurality of pharmacies, from the computing device, and transmit the prescription to be received at the selected pharmacy prescription processing system. The computing device may be a mobile phone, a laptop, or a desktop. The system may also include a mapping component configured to display the plurality of pharmacies on a map.

It is to be understood that both the foregoing general description and the following detailed description are exemplary and explanatory only and are not restrictive of the disclosed embodiments, as claimed.

BRIEF DESCRIPTION OF THE DRAWINGS

The accompanying drawings, which are incorporated in and constitute a part of this specification, illustrate various exemplary embodiments and together with the description, serve to explain the principles of the disclosed embodiments.

FIG. 1 shows a flowchart for transmitting a prescription to a selected pharmacy, according to an embodiment of the present disclosure.

FIG. 7 shows an exemplary list based pharmacy presentation, according to an embodiment of the present disclosure.

FIG. 8 shows a flowchart for updating a pharmacy, according to an embodiment of the present disclosure.

DETAILED DESCRIPTION OF EMBODIMENTS

Figure 2:
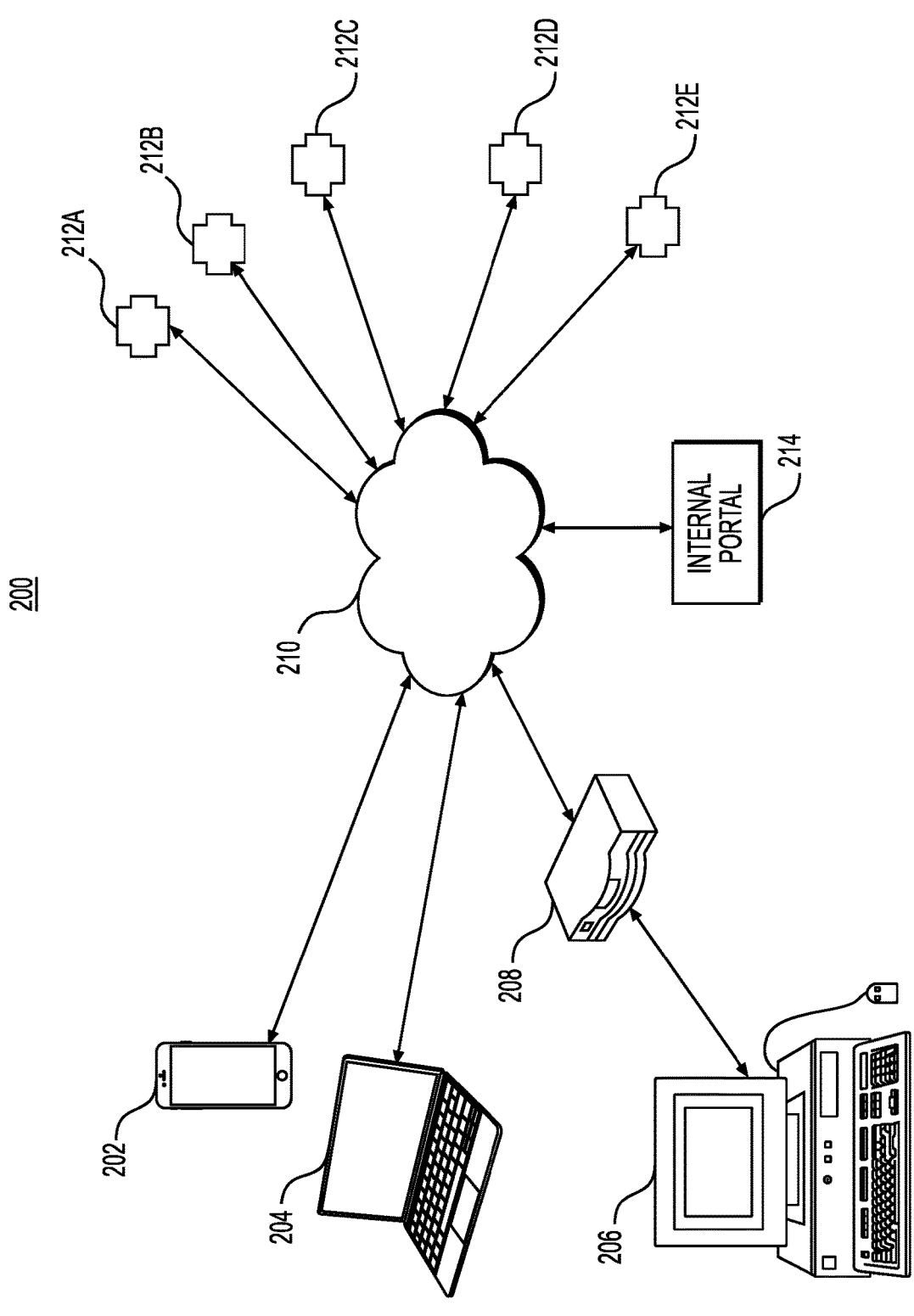
FIG. 2 shows a diagram for a prescription management system, according to an embodiment of the present disclosure.

Embodiments of the disclosed subject matter describe methods and systems for prescription management based on one or more of user information (e.g., user name, user insurance information, user time preference information, discount information, rewards information, review preference information, etc.), location information, prescription(s), treatment availability, pricing information, and the like.

The disclosed subject matter is directed to using electronic components (e.g., computing components, processing components, electronic storage components, cloud services and components, etc.) to identify one or more pharmacies based on user specific factors, and to direct the prescription and user to the one or more pharmacies. The one or more pharmacies are optimally selected for the user via the electronic components. The selection of the one or more pharmacies is based on the availability of specific treatment (e.g., a medicine, a therapy, a device, an application, an object, etc.) at a given pharmacy as well as additional factors such as proximity to a location (e.g., a user's current location or a user's preferred location), pricing information (e.g., user insurance information, discount information, rewards information, etc.), user time preference information, review preference information (e.g., pharmacy rating, similar user experiences, etc.), and the like. The availability of a treatment may refer to whether a pharmacy makes the treatment available to its customers (e.g., whether the treatment is in the pharmacy's inventory system via, for example, a Universal Product Code (UPC) or other designator). Alternatively, the availability of a treatment may refer to whether a unit of the treatment is available at a given pharmacy at a point in time (e.g., if the given pharmacy currently has the treatment in stock).

As further disclosed herein, according to an implementation of the disclosed subject matter, a user and/or a heath care professional may provide a prescription that is received at an electronic system. For example, a user may receive a prescription from a health care professional and may use her mobile device to scan the prescription into a platform connected to the electronic system. Alternatively, for example, a user may request that a health care professional input the prescription directly into a platform (e.g., via a user device, via the healthcare professional device, etc.).

The electronic system may extract relevant information from the prescription including at least the specific treatment (e.g., medicine) associated with the prescription. The electronic system may further identify a location associated with the user. The location may be, for example, the user's current location, a location provided by the user, a dynamically determined location based on user history, and/or a stored location (e.g., user home, user work, etc.). The electronic system may also receive additional user information (e.g., user insurance information, user time preference information, discount information, rewards information, and review preference information). The user information may be provided by the user, stored in memory or in a cloud platform such that it is accessible to the electronic system, or may be determined by the electronic system (e.g., based on user behavior, publically available information, etc.).

The electronic system may identify a plurality of potential pharmacies based on a location criteria (e.g., distance from the given location, a time based criteria, a minimum number of pharmacies based on the given location, etc.). The electronic system may receive treatment availability information and treatment pricing information directly from each of a plurality of location qualifying available pharmacies, from an internet portal, or from one or more third parties, as further described herein. The electronic system may filter the list of available pharmacies based on the treatment availability such that pharmacies that do not have the given treatment available are disregarded. To clarify, pharmacies that do not have the given treatment available may be pharmacies that do not carry the treatment and, accordingly, may not have the treatment available in their inventory systems. According to an alternative implementation, pharmacies that do not have the given treatment available may refer to pharmacies that are out of stock of the treatment.

The electronic system may provide the remaining plurality of pharmacies along with their corresponding treatment pricing information such that the user is able to review the information in an electronic format. For example, the user may access the identified plurality of pharmacies along with their corresponding treatment pricing information via a user device such as a computer or mobile phone. According to an implementation, the user may be provided a map indicating the location (e.g., user location or user preferred location) as well as an indication of the location of each of the plurality of pharmacies. Further, the user may be provided the treatment pricing at each of the plurality of pharmacies. The user may select a pharmacy from the plurality of pharmacies in any applicable manner including via providing the selection using the user device. The selection may be, for example, based on the pharmacy location, the treatment pricing, or one or more other factors. The electronic system may then transmit the prescription to the selected pharmacy such that the user may obtain the corresponding treatment from the selected pharmacy.

According to an implementation, the treatment pricing information may be adjusted by the electronic system such that the adjusted treatment pricing information is presented to the user. The treatment pricing information may be adjusted based on the user information such as the user's insurance information, available or applicable discount information, rewards information, or the like. For example, a given prescription may cost a first amount for a user based on having no insurance policy and may cost a second amount for a user based on an applicable insurance policy. Accordingly, the adjusted pricing information may incorporate insurance discounts based on a user's insurance policy.

According to an implementation, a user may change the selected pharmacy to an updated pharmacy at any time (e.g., during a refill opportunity) based on, for example, a change in location, insurance, pricing, preference, or the like. For example, a user may run out of a given medicine and may require a refill of the medicine. At this time, the user may access the electronic system to identify a pharmacy for submission of the refill prescription. The electronic system may re-analyze the pricing information for the medicine to be refilled at this time and may determine that the originally selected pharmacy's pricing is no longer the best pricing available to the user. Accordingly, an updated pharmacy may be selected by the user based on a presentation of the updated pharmacy via an applicable platform. Based on the selection of the updated pharmacy, the refill prescription may be sent to the updated pharmacy without the user having to request a transfer of the prescription by the health care professional.

The electronic system, as described herein enables integration of electric components and techniques into the practical application of optimal pharmacy selection based on input from various systems (e.g., a prescription submission system, a pharmacy identification system, a pricing analysis system, a location analysis system, a prescription processing system, etc.).

Notably, the techniques disclosed herein cannot practically be performed in the mind and, thus, require some or all of the components of the electronic system, as disclosed herein. For example, the techniques disclosed herein include identifying, via one or more processors, a plurality of pharmacies based at least on availability of a treatment (e.g., based on the pharmacies carrying the treatment and/or based on the pharmacies having the treatment in stock). At the very least, such a task is not practical to be performed in the mind as it would require patching into the electronic systems of a possibly unlimited number of pharmacies to determine availability. Further, for example, the techniques disclosed herein include adjusting pricing information based on user information. Such an adjustment requires near real time analysis based on information from multiple pharmacies as well as one or more other systems (e.g., an insurance system). Such a task is certainly not practical to be performed in the mind especially when considering that each prescribed treatment may require its own different subset of analysis.

Additionally, the electronic system and the techniques disclosed herein provide a number of technical benefits. For example, the electronic system operates in a manner similar to a "wallet" such that it stores a given prescription as the pharmacy selection analysis is performed and continues to store it thereafter. The user may be able to apply the stored prescription at a later time with an updated analysis, rather than the user having to reach out to the medical professional for a change in use of the prescription. Additionally, the electronic system and techniques disclosed herein enable the pharmacy selection optimization, as described herein, and integrates the optimization with a direct submission of the prescription to the selected pharmacy's prescription processing system. Additionally, the electronic system and techniques disclosed herein enable a user to easily determine costs of a treatment or product, with and/or without coverage, determine potential generic versions that may be cheaper, determine potential alternative prescription therapies, transfer prescriptions to different pharmacy locations, add or change insurance information/coverage plans, submit prescription refills to different pharmacy locations, and/or start or pause automatic prescription refills.

The subject matter of the present disclosure will now be described more fully hereinafter with reference to the accompanying drawings, which form a part hereof, and which show, by way of illustration, specific exemplary embodiments. An embodiment or implementation described herein as "exemplary" is not to be construed as preferred or advantageous, for example, over other embodiments or implementations; rather, it is intended to reflect or indicate that the embodiment(s) is/are "example" embodiment(s). Subject matter may be embodied in a variety of different forms and, therefore, covered or claimed subject matter is intended to be construed as not being limited to any exemplary embodiments set forth herein; exemplary embodiments are provided merely to be illustrative. Likewise, a reasonably broad scope for claimed or covered subject matter is intended. Among other things, for example, subject matter may be embodied as methods, devices, components, or systems. Accordingly, embodiments may, for example, take the form of hardware, software, firmware, or any combination thereof. The following detailed description is, therefore, not intended to be taken in a limiting sense.

Throughout the specification and claims, terms may have nuanced meanings suggested or implied in context beyond an explicitly stated meaning. Likewise, phrases such as "in one embodiment" or "according to an implementation" as used herein does not necessarily refer to the same embodiment or implementation and the phrase "in another embodiment" or "in another implementation" as used herein does not necessarily refer to a different embodiment or implementation. It is intended, for example, that claimed subject matter include combinations of example embodiments and implementations, in whole or in part.

The terminology used herein may be interpreted in its broadest reasonable manner, even though it is being used in conjunction with a detailed description of certain specific examples of the present disclosure. Indeed, certain terms may even be emphasized; however, any terminology intended to be interpreted in any restricted manner will be overtly and specifically defined as such in this Detailed Description section.

As used herein, a pharmacy may refer to any physical location (e.g., a pharmacy store, a dispensary, a building, etc.), an office (e.g., a fluid test location, a medical procedure office, etc.), a virtual portal (e.g., a website, an application, a telemedicine setup, direct to consumer or direct to user setup, etc.), or any other entity or location configured to provide treatments.

As used herein, a treatment may refer to anything that can be obtained from a healthcare facility and may include, but is not limited to, medicine, a procedure, a therapy, a device, an application, an object, or the like, or combinations thereof.

As used herein, a user may refer to a patient, an animal, an individual, or a group of individuals and also may refer to any third party (e.g., spouse, relative, caretaker, robot, etc.) that may facilitate all or part of the process of obtaining a treatment for an individual or group of individuals.

FIG. 1 shows a flowchart 100 for transmitting a prescription to a selected pharmacy, according to at least one aspect of the present disclosure. FIG. 2 shows a diagram for a prescription management system, according to at least one aspect of the present disclosure. FIG. 2 is used herein to show an example implementation of flowchart 100 of FIG. 1 and a flowchart 800 of FIG. 8. FIG. 2 includes a mobile device 202, a laptop 204, a desktop 206, a server 208, a cloud electronic system 210, a plurality of pharmacies 212A, 212B, 212C, 212D, and 212E, and an internet portal 214. It will be understood that one or more steps of flowchart 100 may be performed simultaneously or in an order different than that shown in FIG. 1. The order shown in FIG. 1 is for convenience only, and is not meant to show the only order that the techniques disclosed herein can be performed.

The implementations disclosed herein may be performed by an electronic system which includes, for example, a cloud electronic system 210 of FIG. 2 as well as one or more other components of FIG. 2, as shown and further discussed herein. The electronic system may have one or more processors, storage, ports, inputs, outputs, buses, and the like, configured to perform methods described in this disclosure. The electronic system may include or may interact with a machine learning model, transmission components, and receiving components, which may each be software, firmware, or hardware components stored in the computer system. The electronic system may be configured to utilize the machine learning model and/or transmission components and receiving components when performing various methods described herein. The machine learning model may be a plurality of machine learning models. According to an implementation, a plurality of pharmacies may be identified using a trained machine learning model. The trained machine learning model may be trained based on pharmacy and treatment specific historical data and/or based on historical user pharmacy selection data. Inputs to the trained machine learning model may be one or more of user information, the location, prescription information (e.g., treatment, refill information, alternative treatment information, etc.).

Although a single component is shown to represent cloud electronic system 210 in FIG. 2, it will be understood that cloud electronic system 210 may include scalable resources for computation and/or data storage, and may run one or more applications to perform various computer-implemented techniques described herein.

Cloud electronic system 210 may be configured to receive data from other components (e.g., consumers, third party applications, and/or devices) of the system environment via a network such as internet portal 214 of FIG. 2. Cloud electronic system 210 may further be configured to utilize the received data by inputting the received data into a machine learning model to produce a result (e.g., a plurality of pharmacies, a ranked order of pharmacies based on multiple factors, etc.). Information indicating the result may be transmitted to a user device over the network such as internet portal 214 of FIG. 2. In some examples, cloud electronic system 210 may be referred to as a server system that provides a service including providing the information indicating the result to a user. Additionally, a user device (e.g., mobile device 202, laptop 204, desktop 206, etc.) may operate a client program, also referred to as a platform, used to communicate with cloud electronic system 210. This platform may be used to provide information to cloud electronic system 210 and/or to receive information from cloud electronic system 210. In some examples, the platform may be a mobile application that is run on mobile device 202 operated by the user. The platform may be a mobile application, desktop application, software, website, cloud service, etc.

User devices (e.g., mobile device 202, laptop 204, desktop 206, wearable devices, tablets, holograms, etc.) may each be an electronic system. User devices may be capable of transmitting information indicating a current location of the device, as further disclosed herein at step 104 of FIG. 1. For example, a user device may have an application configured to transmit data indicating a current location of the mobile device to cloud electronic system 210, based on a GPS translocator located at the user device.

As shown in FIG. 1 at step 102, user information may be received at an electronic system such as cloud electronic system 210 of FIG. 2. Although cloud electronic system 210 will be referenced herein, it will be understood that cloud electronic system 210 may reference any electronic system with one or more cloud components and/or one or more local components. The user information may be any information and/or data related to a user and may include, but is not limited to, user insurance information, user time preference information, discount information, rewards information, and review preference information, or the like. The user information may be information that is provided by the user or may be information about or related to the user that is obtained, determined, or otherwise provided by a third party. The user information may be received by cloud electronic system 210 and may be provided via user devices such as one or more of mobile device 202, laptop 204, desktop 206, server 208, or the like. Alternatively, all or a portion of the user information may be obtained from the internet portal 214. The user information received at step 102 may be stored locally, such as at mobile device 202, laptop 204, desktop 206, or server 208, or may be stored at cloud electronic system 210 or an associated component such as a memory or database, as further described herein.

User insurance information may be the user's insurance company's identification information (e.g., Blue Cross Blue Shield®), a member number, a group number, a telephone number, a plan identifier, plan details, plan network details, or the like. For example, the user insurance information may include details about prescription co-pays for the user's specific insurance plan. As another example, the user insurance information may include the brand name coverage vs. generic coverage provided via the user's insurance plan. For example, a user may input the user's insurance member number using an application on mobile device 202. Cloud electronic system 210 may receive the member number and may obtain specific insurance information, including covered prescription costs, based on the member number by accessing internet portal 214.

User time preferences may be preferences based on times that the user prefers to obtain a given treatment from a pharmacy, wait times at a pharmacy, operating hours of a pharmacy, times that a delivery of a treatment can be made, or the like.

Discount information and/or rewards information may be information that enables a reduction in pricing for a treatment, provides a non-monetary incentive related to the purchasing or acquisition of the treatment, or provides a future benefit associated with the purchasing or acquisition of the treatment. As an example, cloud electronic system 210 may access internet portal 214 to identify any coupons, rebates, discount codes, discount programs, or the like, associated with a given prescribed treatment. In some examples, a treatment price may include discounts available to the user. For example, pharmacies may have coupons, rewards programs, etc., that can lower the cost of prescription drugs. In other examples, coupons and discounts may be provided through a given platform (e.g., mobile application) itself. According to this example, a user may receive a discount on the treatment by fulfilling the prescription through the platform used to identify pharmacies, as disclosed herein.

Review preference information may be any user preferences based on the quality, credibility, ease of use, prior interaction, or the like based on a given pharmacy. The review preference information may include, for example, a minimum rating, a rating based on the same or similar treatments obtained via a given pharmacy, a recent rating, or the like. The review preference information may be user provided or may be determined by cloud electronic system 210.

At step 104 of FIG. 1, a location may be received. The location may be received by cloud electronic system 210 of FIG. 2 and may be provided via one or more of mobile device 202, laptop 204, desktop 206, or server 208. The location may be input by a user (e.g., by providing all or part of an address), may be selected from a plurality of previously provided locations (e.g., home or work), or may be dynamically determined. A location may be dynamically determined using any applicable technique such as cellular triangulation, a global positioning system (GPS), Bluetooth® pairing, or any other tracking technique. Alternatively, the location may be obtained via internet portal 214 based on accessing a user account that may include user preferences and/or user location information.

The location received at step 104 may be stored locally, such as at mobile device 202, laptop 204, desktop 206, or server 208, or may be stored at cloud electronic system 210 or an associated component such as a memory or database, as further described herein.

At step 106 of flowchart 100 of FIG. 1, a prescription, associated with the user information received at step 102, is received. Step 106 is performed via a prescription submission system which can include one or more of a user device, an API to port the prescription to cloud electronic system 210, an optical character recognition software and/or a prescription format specific recognition software, and the like. The prescription may include a treatment (e.g., a medicine, a therapy, a device, an application, an object, etc.) and may be submitted electronically or may be a physical copy that is scanned and provided to cloud electronic system 210.

According to an implementation, a healthcare professional may provide the prescription such that it can be received by cloud electronic system 210. The healthcare professional may provide the prescription via a platform using a user device such as the user's mobile phone (e.g., mobile device 202), via a computer (e.g., laptop 204), desktop 206, or the like. As an example, a healthcare professional may upload the prescription via desktop 206 at the healthcare professional's office. The desktop 206 may transmit the uploaded prescription to server 208 (e.g., a secure server, a Health Insurance Portability and Accountability Act (HIPPA) compliant server). Server 208 may then transmit the prescription, either individually or with a batch of prescriptions, to cloud electronic system 210. Cloud electronic system 210 may associate the prescription with user information (e.g., the user's name or an identification number), and retrieve additional data from the prescription.

Figure 3:
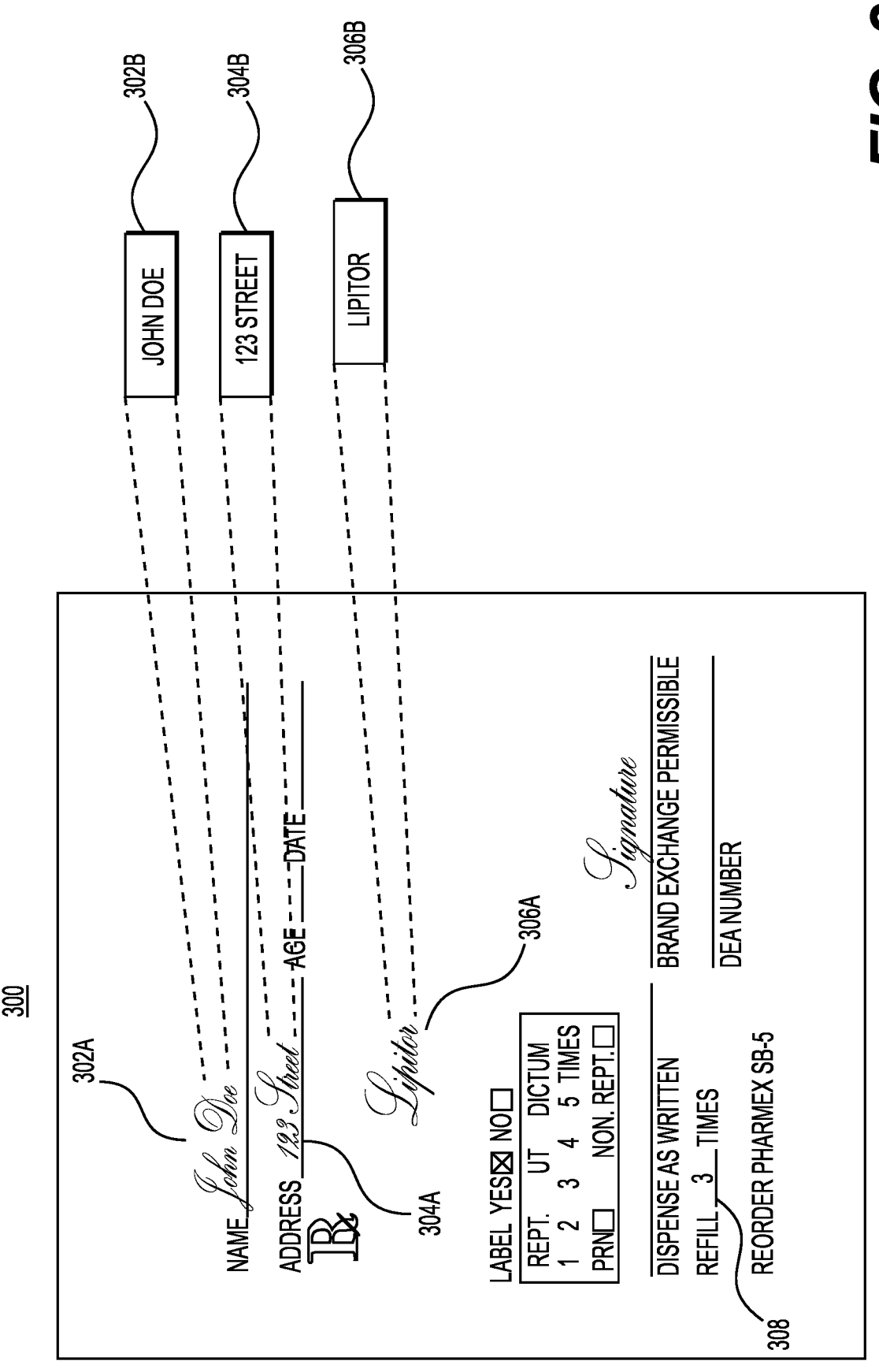
FIG. 3 shows an exemplary prescription and associated data retrieval, according to an embodiment of the present disclosure.

FIG. 3 shows an example prescription 300 and associated data retrieval based on prescription 300. Prescription 300 may be provided by a health care professional in a tangible or scanned format. Prescription 300 (e.g., a physical prescription) may be provided during a physical visit, via mail, via electronic communication (e.g., a scan via email), or the like. Prescription 300 may be provided to cloud electronic system 210 at step 106 of flowchart 100 of FIG. 1. According to an implementation, a user may scan the physical prescription using an independent camera or scanner or via a camera attached to a user device such as mobile device 202. The scan may be accessed directly by an application or other software associated with cloud electronic system 210. Alternatively, an already scanned prescription (e.g., a prescription sent via email, or scanned using a device and stored in memory) may be uploaded to the application or other software associated with cloud electronic system 210.

As shown in FIG. 3, prescription 300 may include user information such as user name 302A and user address 304A. Prescription 300 may also include a treatment 306A as well as refill information 308. User information including user name 302A and user address 304A, treatment 306A, and refill information 308 may be received by cloud electronic system 210 via, for example, a platform (e.g., an application, other software, etc.).

The platform or the cloud electronic system may retrieve the information included in prescription 300. An optical character recognition software and/or a prescription format specific recognition software may be used to extract the information included in prescription 300. The information included in prescription 300 may be extracted and converted into an electronic format including, for example, an electronic name 302B, an electronic address 304B, and an electronic treatment 306B. Additional information such as prescription strength and quantity may also be retrieved from a prescription provided to cloud electronic system 210 (e.g., based on a user or healthcare provider input or via extracting the information from a physical or scanned prescription such as prescription 300).

Upon receiving a prescription, at step 106 of FIG. 1, the prescription may be stored via cloud electronic system 210, for use by the user. In other words, cloud electronic system 210 may serve as a virtual wallet to hold one or more of the user's prescriptions such that they can be accessed and managed via a single platform associated with cloud electronic system 210. This configuration may allow the user to easily access all of her prescriptions through the single platform. The user may access her virtual wallet to select each prescription individually when she is preparing to fulfill or refill the prescription.

Figures 4A, 4B:
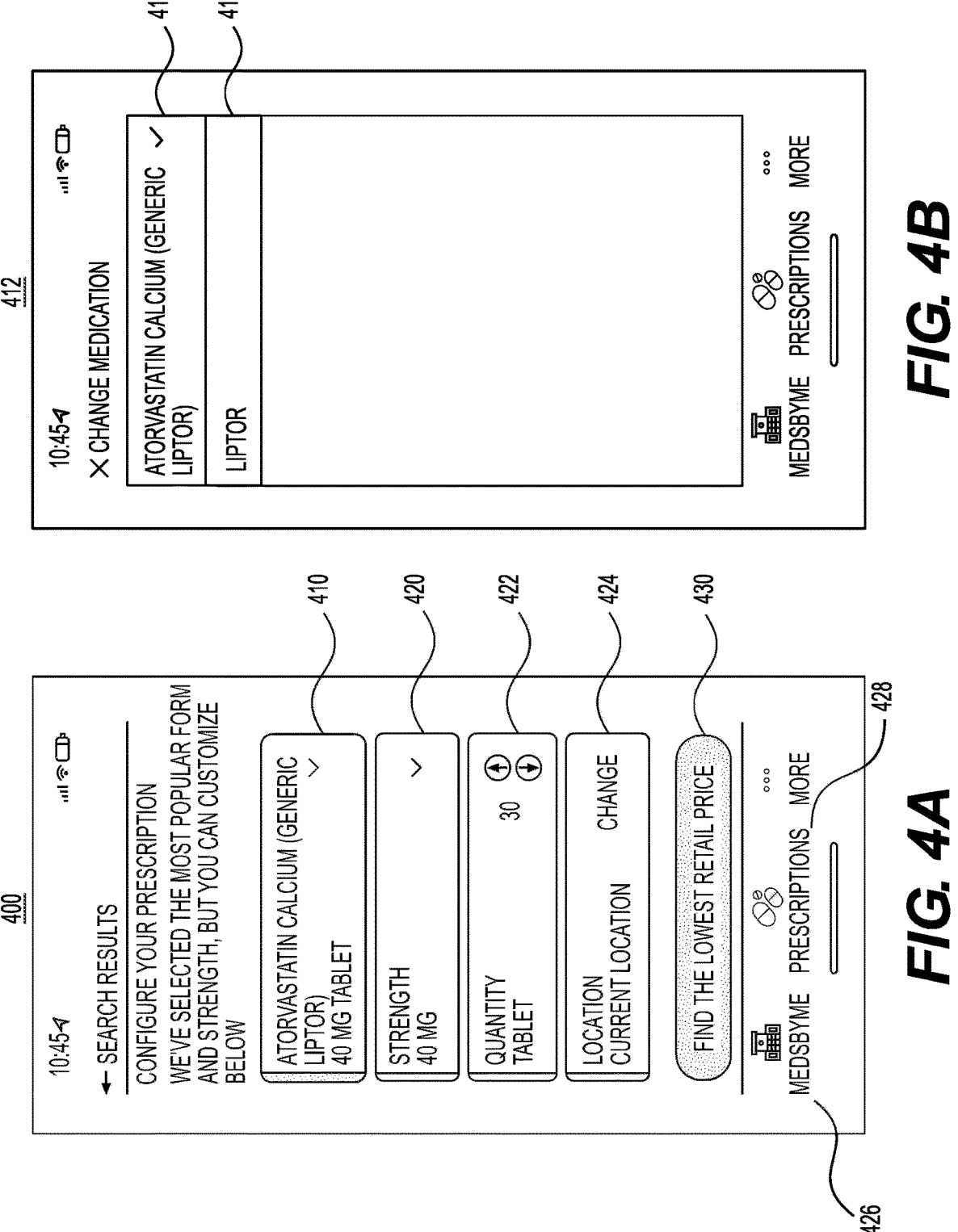
FIG. 4A shows an exemplary graphical user interface (GUI) of a prescription configuration, according to an embodiment of the present disclosure.
FIG. 4B shows an exemplary alterative treatment selection, according to an embodiment of the present disclosure.

Upon receiving a prescription, at step 106 of flowchart 100 of FIG. 1, cloud electronic system 210 may enable the user to access her prescription information via an associated platform such as an application or other software. FIG. 4A shows an example platform with a prescription page 400. As shown, prescription page 400 includes a treatment 410, a strength information 420, a quantity 422, a location 424, as well as a submission button 430.

The treatment 410 may be based on the prescription provided electronically by the healthcare professional, input electronically by the user, scanned, or uploaded. For example, prescription 300 of FIG. 3 may be scanned and the written treatment 306A on prescription 300 may be converted to electronic treatment 306B. Electronic treatment 306B may be used to generate the treatment 410 within the prescription page 400 shown in FIG. 4A. Similarly, strength information 420 and quantity 422 may be accessed via prescription page 400 of the platform. As also shown in FIG. 4A, the user may be provided additional options via prescription page 400 such as a home page option 426 to return to a user account page and a prescriptions option 428 to view all of the user's prescriptions that have been uploaded to be accessed via the platform.

For medical conditions for which there are multiple effective prescription medications, healthcare professionals may select a medication to prescribe based on one or more criteria (e.g., price, ease of use in terms of form, number of uses, and/or duration of treatment). Alternative treatments can be presented and may allow a user to compare the price of the prescribed treatment to effective substitutes. According to an implementation, a platform (e.g., an application, other software, etc.) or cloud electronic system 210 of FIG. 2 may determine one or more alternative treatments based on a given treatment (e.g., provided via a prescription). The one or more alternative treatments may be substitutes for the given treatment and may be, for example, a generic or brand name medicine associated with the treatment, a generic or brand name medicine not associated with the treatment, an alternative therapy, a medical device, or the like. For example, a healthcare professional may prescribe a given medicine to the user. The user may upload the prescription to cloud electronic system 210 and cloud electronic system 210 may access internet portal 214 to determine that a generic version of the medicine is available on the market. The alternative treatments may be determined based on a database configured to provide alternative treatment information. The database may be accessed by or may be part of cloud electronic system 210 directly, may be accessed via internet portal 214, or the like, and/or may be a third party database.

According to an implementation, cloud electronic system 210 may automatically provide the user with the cheapest option between the prescribed treatment and an alternative treatment. Alternatively, the user may be presented with an option to elect from two or more options between the prescribed treatment and one or more alternative treatments. For example, the user may select treatment 410 of FIG. 4A to access a treatment change page 412, as shown in FIG. 4B. Treatment change page 412 may include multiple options including the given treatment 414 as well as one or more alternative treatments such as alternative treatment 416. The user may select any of the options provided on treatment change page 412.

At step 108 of flowchart 100 of FIG. 1, a plurality of pharmacies may be identified based on the availability of a treatment and/or an alternative treatment and a location criterion. Cloud electronic system 210 may determine which pharmacies, from an available number of pharmacies, meet the location criterion based on the location received at step 104 of FIG. 1. The location criterion may be used to filter the available number of pharmacies to a subset of the available number of pharmacies, based on their locations. According to an implementation, the location criterion may be used to filter the available number of pharmacies to a subset of the available number of pharmacies, based on the locations that the pharmacies can ship or otherwise transport a given treatment. The location criterion may be a distance proximity, a time proximity, a minimum number of pharmacies, and/or the like. The location criterion may be a factor of multiple criteria such as, for example, a distance proximity in combination with a time proximity.

A distance proximity may be a threshold physical distance calculated from a given location (e.g., the location received at step 104 of flowchart 100). The threshold physical distance may be determined based on user input (e.g., the user may provide a maximum distance from the location via a platform), may be determined dynamically based on, for example, a density of pharmacies around the location, may be determined based on past or stored preferences, or the like. Pharmacies that meet the distance proximity may be pharmacies that are within a distance from the location (e.g., the location received at step 104 of flowchart 100) that is below the threshold physical distance.

A time proximity may be a threshold time to reach a pharmacy from a given location (e.g., the location received at step 104 of flowchart 100). The threshold time may be determined based on user input (e.g., the user may provide a maximum time from the location to a pharmacy, via a platform), may be determined dynamically based on, for example, traffic patterns, may be determined based on past or stored preferences, or the like. Additionally, the time to reach a pharmacy may be determined based on a preferred, stored, or previously used mode of transportation. For example, a user my input, or it may be determined, that the user is or can traverse via a motorized vehicle, by walking, by biking, via public transportation, or the like. Accordingly, a list of pharmacies may be filtered based on the time proximity from the location to each of the pharmacies based on a preferred or selected mode of transportation. Pharmacies that meet the time proximity may be pharmacies that can be reached, from the location, within the threshold time.

A minimum number of pharmacies based location criterion may be applied such that a minimum threshold number of pharmacies from a given location are provided despite the distance and/or time from the location. Notably, the minimum number of pharmacies location criterion may be applied to ensure that a user is provided with enough options for pharmacies to make an informed decision when selecting a pharmacy. The minimum number of pharmacies may be selected by the user, may be predetermined or stored, or may be dynamically determined based on the user's history. To clarify, the minimum number of pharmacies may be selected based on one or more of the distance proximity or the time proximity criteria such that the closest pharmacies up to the minimum number of pharmacies are provided. As an example, the difference between the distance proximity and the minimum number of pharmacies criteria is that the distance proximity criterion may result in one or no pharmacies (e.g., if only one or no pharmacy meets the distance threshold), whereas the minimum number of pharmacies criteria will result in the number of pharmacies identified in the minimum number of pharmacies criterion, even if some of the pharmacies are a very large distance (e.g., one hundred miles) away.

As shown in diagram 200 of FIG. 2, cloud electronic system 210 may be in direct communication with multiple pharmacies 212A through 212E According to an alternative implementation (not explicitly shown), cloud electronic system 210 may connect to the multiple pharmacies 212A through 212E via internet portal 214. In either implementation, at step 108 of FIG. 1, the electronic system 210 may identify whether a treatment is available at each pharmacy from the multiple pharmacies that meet a location criterion. The electronic system 210 may identify whether a treatment is available at a given pharmacy by receiving communication from the given pharmacy regarding the availability status of the treatment, by receiving communication from a third party, and/or by referencing a previously provided or retrieved availability status.

According to an implementation, the availability status may indicate whether or not a given pharmacy carries the treatment. Such an indication may be provided by, for example, a look up table that includes a list of all the treatments that the pharmacy is associated with. Such an indication may be provided by, for example, matching a code associated with the treatment (e.g., a UPC code, a National Drug Code (NDC), a Drug Identification Number (DIN), etc.), with a list of codes for treatments that the pharmacy carries.

According to another implementation, the availability status may also indicate whether or not a given pharmacy has the treatment in stock. Such an indication may be provided via a pharmacy's supply chain management system or any other tracking system that includes information regarding the pharmacy's inventory at a given time or a projected time.

According to an implementation, cloud electronic system 210 may identify the availability of a given treatment by patching into a given pharmacy's treatment management system via, for example, an application programming interface (API) that enables cloud electronic system 210 to retrieve information from the pharmacy's treatment management system. Alternatively, cloud electronic system 210 may identify the availability of a given treatment via a third party system that may accumulate treatment information from one or more pharmacies and may make that information available to cloud electronic system 210.

According to an implementation, cloud electronic system 210 may identify the availability of a given treatment at a given pharmacy based on identifying the treatment pricing information from the given pharmacy. For example, if cloud electronic system 210 identifies the treatment pricing information for a given treatment to be $0 or a negative value, the $0 or negative value may indicate that the given treatment is either not sold at the pharmacy or is out of stock at the pharmacy.

At step 110 of flowchart 100 of FIG. 1, the treatment pricing information for each of the pharmacies identified at step 108 of FIG. 1 may be identified. It will be understood that although step 110 is shown as being subsequent to step 108 in FIG. 1, step 110 may also be performed simultaneously to or prior to step 108 such that the treatment pricing information and the availability information may be identified at the same time, or the treatment pricing information may be identified prior to the treatment availability information.

Cloud electronic system 210 may obtain treatment prices by patching into a given pharmacy's treatment management system via, for example, an API that enables cloud electronic system 210 to retrieve pricing information from the pharmacy's treatment management system. Alternatively or in addition, cloud electronic system 210 may obtain treatment pricing information from third-parties, such as the Associated Pharmacies, Inc., the warehouse subsidiary of American Associated Pharmacies (AAP), pharmacy benefit managers, independent pharmacies or pharmacy chains, or drug discount card programs. According to an implementation, at step 110 of flowchart 100, additional information on the prescribed treatment, such as the brand name of a medicine, the manufacture of the drug, the generic name of the drug and/or alternative prescription therapies, if any, and/or the dose and dosage amounts may also be pulled from each of the pharmacies and/or the third parties.

According to an implementation, cloud electronic system 210 may adjust the retrieved pricing information (i.e., treatment pricing for each pharmacy) based on user information (e.g., as described at step 102 of FIG. 1). For example, cloud electronic system 210 may adjust the retrieved pricing information based on one or more of user insurance information, discount information, rewards information, or the like. Notably, the retrieved pricing information may be adjusted to reflect an actual price that the user would need to pay to obtain the treatment. As an example, the electronic system 210 may receive a user's insurance information at step 102 of FIG. 1 and may identify the treatment pricing information at step 110. Based on the user insurance information and the treatment pricing information, a determination may be made that the user insurance would cover 50% of the cost of the treatment. Accordingly, the treatment pricing information may be updated to be 50% of the cost initially identified at step 110.

Figure 5:
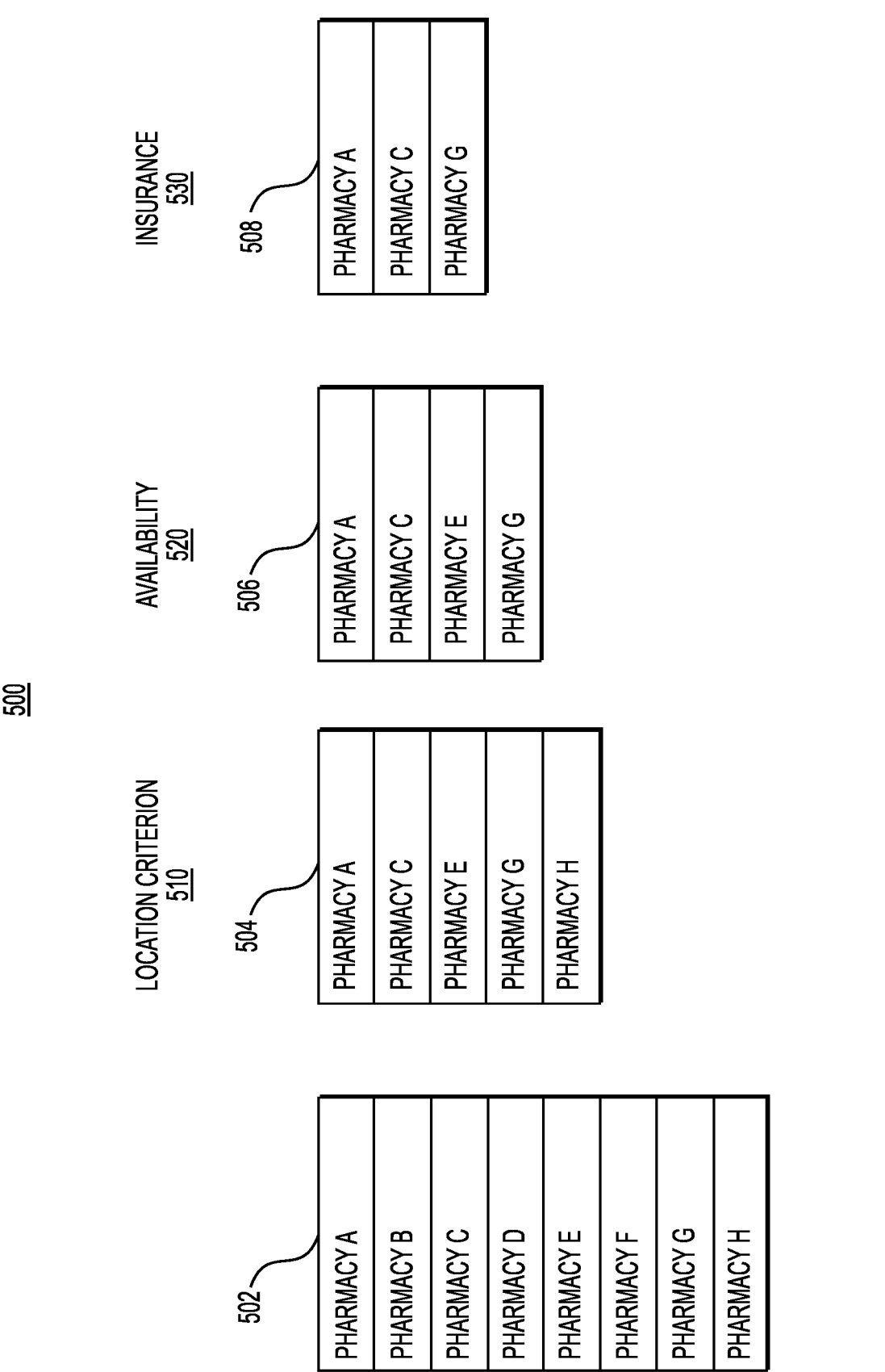
FIG. 5 illustrates an exemplary decision tree for pharmacy selection, according to an embodiment of the present disclosure.

FIG. 5 shows an example decision tree 500 including multiple tables, each table including pharmacies present after a given filter is applied based on steps 102 through 110 of FIG. 1, as disclosed herein. As shown, a cloud electronic system 210 may initiate the pharmacy decision process by starting with a full set of available pharmacies as shown in table 502. The full set of available pharmacies of table 502 may be filtered to the table 504 based on a location criterion 510 as applied at step 108, based on the location received at step 104 of FIG. 1. The pharmacies in location criterion 510 filtered table 504 may be a subset of the available pharmacies in table 502. The filtered pharmacies in table 504 may further be filtered based on an availability decision 520, resulting in the filtered table of pharmacies at table 506. Availability decision 520 may filter the pharmacies based on whether a given treatment is available at the pharmacy (e.g., if the treatment is sold at the pharmacy or if the treatment is in stock at the pharmacy). Similarly, the filtered pharmacies in table 506 may further be filtered based on whether the pharmacies accept the user's insurance at insurance decision 530, resulting in the filtered table of pharmacies at 508. Accordingly, the filtered list of pharmacies 508 may include the pharmacies that are presented to the user, as further disclosed herein, based on one or more of the location criterion 510, treatment availability decision 520, and insurance decision 530. It will be understood that although FIG. 5 shows an example decision tree 500 including specific filters, the filters may vary based on implementations of the disclosed subject matter. Additionally, although the filters are shown to be applied in a given order in the example shown in FIG. 5, the filters may be applied simultaneously or may be applied in any order.

At step 112 of flowchart 100 of FIG. 1, a plurality of pharmacies and the corresponding pricing information for a given treatment at each of those plurality of pharmacies may be transmitted. Notably, the plurality of pharmacies transmitted at step 112 may be the pharmacies that meet at least the availability and the location criterion as described at step 108 and may also meet one or more other criterion such as, but not limited to, user information based criterion, maximum price, etc. The transmission may be made via cloud electronic system 210 and may be received by a user using a user device such as mobile device 202, laptop 204, and/or desktop 206.

Figure 6:
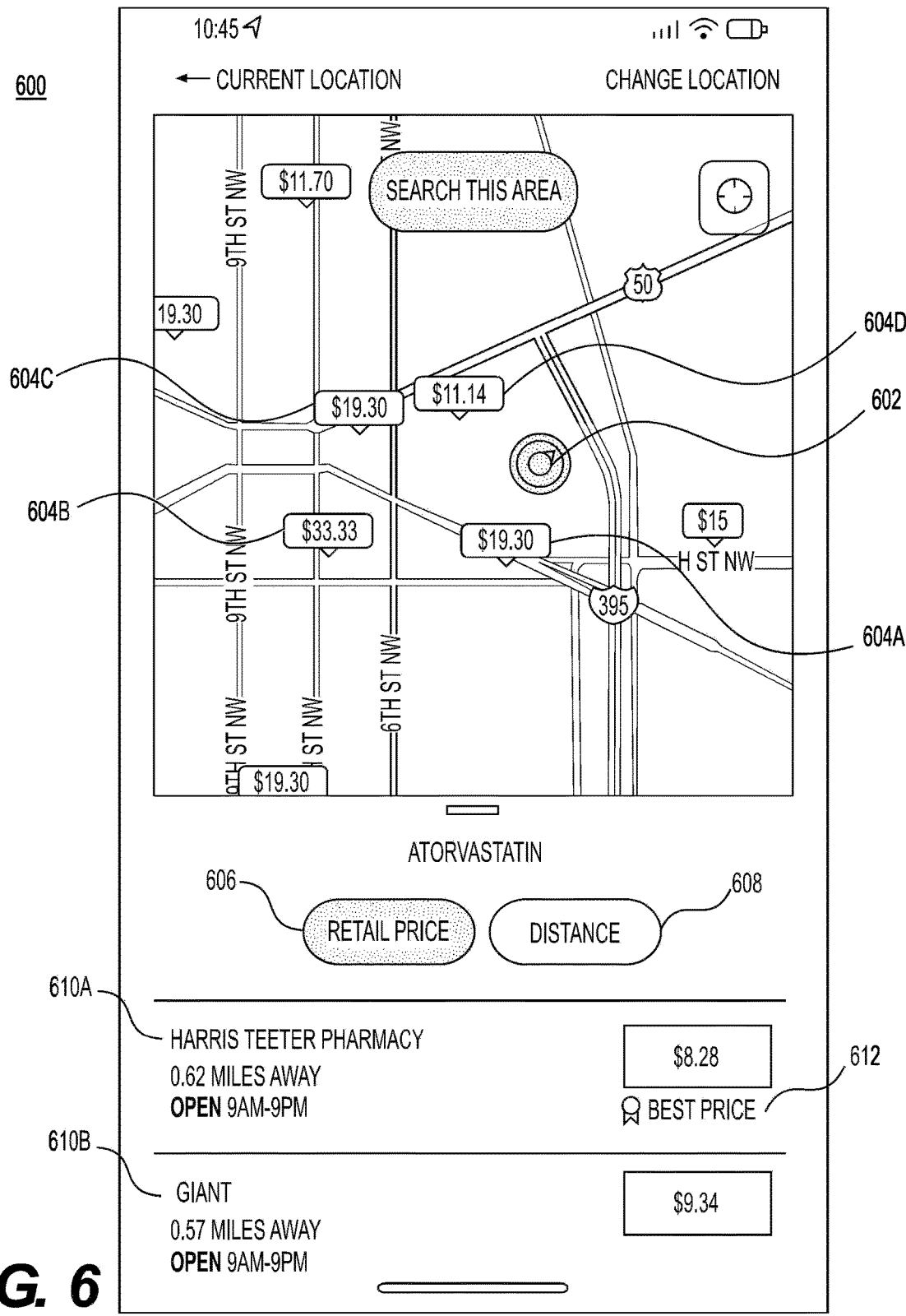
FIG. 6 shows an exemplary graphical user interface (GUI) of a map based pharmacy presentation, according to an embodiment of the present disclosure.

According to an implementation, the plurality of pharmacies and their corresponding treatment pricing information may be transmitted, at step 112, such that it may be viewed on a user device (e.g., mobile device 202, laptop 204, and/or desktop 206) in a map format, as shown in FIG. 6, a list format, as shown in FIG. 7, or in any other applicable format that may enable a user to select a pharmacy.

A plurality of pharmacies transmitted at step 112 may be viewed in a map format that visually shows the plurality of pharmacies overlaid or otherwise identified on a map. The plurality of pharmacies may be shown relative to the location received at step 104 of FIG. 1. The location received at step 104 of FIG. 1 may also be overlaid or otherwise identified on the map. Additionally, the pricing information for the given treatment received via the prescription, at step 106, may also be provided on or around the map such that the user can easily understand the pharmacy options and their corresponding prices for a given treatment.

FIG. 6 shows an example map 600 that includes a user's current location 602 as well as a plurality of pharmacies 604A, 604B, 604C, and 604D. Each of the plurality of pharmacies 604A-604D may meet a location criteria (e.g., within 5 miles from location 602), may meet a time proximity criteria (e.g., within 20 minutes from location 602 by bike), may meet a minimum number of pharmacies criteria (e.g., at least four pharmacies), may have the respective treatment available at the pharmacy, may be open during a time provided by the user (e.g., via user information collected at step 102), may accept the user's insurance, and the like, as disclosed herein. Additionally, as shown in map 600, the price for the given treatment, at each corresponding pharmacy, may be overlaid on the map 600 at the location (i.e., pharmacies 604A-604D) of the corresponding pharmacy. As also shown in FIG. 6, the map 600 may be supplemented by a list of pharmacies 610A and 610B corresponding to the pharmacies shown on the map 600. For example, the listed pharmacy 610A may correspond to the pharmacy 604A's location shown on the map 600. A user may be able to select a sort order by selecting "Retail Price" using button 606 or by selecting "Distance" using button

608. Selection of "Retail Price" using button 606 may order the list of pharmacies in order of price and selection of "Distance" using button 608 may order the list of pharmacies in order of distance from location 602. As also shown in FIG. 6, a "Best Price" indicator 612 may be provided to indicate the lowest price available from the identified plurality of pharmacies.

FIG. 7 shows an example table 700 of a plurality of pharmacies transmitted at step 112. The list view shown in FIG. 7 may be used, for example, when a user device does not have sufficient bandwidth to load the map view of FIG. 6. As shown, the list view may provide the plurality of pharmacies transmitted at step 112 in column 702, their corresponding distances from a location (e.g., user location or preferred location) at column 704, and the price for the treatment at column 706. The user may sort the list via interaction with any of the columns 702, 704, or 706 by, for example, selecting the title of the respective column. Selecting column 702 may sort the table 700 alphabetically based on the name of the pharmacies. Selecting column 704 may sort the table 700 based on the distance of each pharmacy from a location. Selecting column 706 may sort the table 700 based on the price of the treatment.

At step 114 of flowchart 100 of FIG. 1, a selection of a pharmacy may be received. The pharmacy may be selected by the user by interaction with a user deice (e.g., by selecting a pharmacy in map 600 of FIG. 6 or via a row in table 700 of FIG. 7). One or more confirmations may be received prior to the selection being finalized. For example, a user may select a pharmacy and may be directed to an electronic confirmation page where details about the pharmacy (e.g., location, hours of operation, distance, etc.) as well as the treatment (e.g., medicine name, quantity, strength, etc.), may be provided. The user may confirm the information and, upon confirmation, finalize the selection of the pharmacy.

At step 116 of flowchart 100 of FIG. 1, the prescription received at step 106 may be transmitted to the pharmacy selected at step 114. The prescription may be transmitted by cloud electronic system 210 either directly to the pharmacy selected at step 114, may be transmitted via internet portal 214, or may be transmitted via a third party service and/or equipment. The prescription may be transmitted such that a prescription processing system at the pharmacy selected at step 114 is able to receive the prescription and such that the prescription is fulfilled by the pharmacy as if the prescription was sent directly from the healthcare provider that initiated the prescription. Upon transmitting the prescription to the selected pharmacy, at step 116, the user may receive a confirmation of the transmission of the pharmacy. The user may then be able to visit the pharmacy to pick up the treatment associated with the prescription. Alternatively, the pharmacy may be able to ship the treatment associated with the prescription directly to the user.

Notably, the process described in flowchart 100 of FIG. 1 and, specifically, transmitting the prescription to the selected pharmacy, at step 116, is different from conventional methods of fulfilling prescriptions. The process described in flowchart 100 enables a user to easily control when and where she can submit her electronic prescriptions. As discussed herein, conventional prescription fulfillment requires a user to provide the healthcare professional with a pharmacy location. The user must do this before assessing the location, benefits, or potential costs of a prescribed treatment. However, as disclosed herein, the treatment from a given prescription may be placed into a queue within the system until the user accesses the system (e.g., the treatment may be held in a virtual "wallet"), inputs relevant data, reviews the results, and selects a pharmacy to fulfill the prescription.

Although a single treatment is generally discussed in reference to FIG. 1, it will be understood that the techniques disclosed herein may be applied to multiple treatments via one or more prescriptions. The multiple treatments may be stored in the "virtual" wallet for future reference and/or use.

Additionally, based on the disclosed subject matter, a user may update the list of pharmacies based on a change in circumstance (e.g., change in time, an upcoming refill, change in insurance, etc.). For example, once a refill is needed, the system may identify a new plurality of pharmacies based on updates to the user information and/or pharmacy data, such as new or closed pharmacy locations and updated pricing information. The user may then decide to submit her subsequent refills to an updated pharmacy other than the originally selected pharmacy to which the original request was sent. In some cases, the home or office location of the user may change, so that the user may need to pick a more convenient pharmacy location for her next refill. In other cases, the user may change their pharmacy before each refill to take advantage of the best pricing. This benefit is advantageous since prices of pharmaceutical treatments fluctuate frequently, based on various circumstances and decisions made by third-parties, such as pharmaceutical companies, healthcare companies, and pharmacy benefit managers.

FIG. 8 shows a flowchart 800 for identifying an updated pharmacy to receive a follow-up treatment (e.g., a refill). A user may access a list of stored treatments via a user device (e.g., mobile device 202, laptop 204, desktop 206 of FIG. 2, etc.). The list of stored treatments may be previously provided treatments extracted from the process described in FIG. 1 via flowchart 100. Notably, the list of stored treatments may be treatments that are provided via one or more prescriptions and received by cloud electronic system 210 of FIG. 2. The stored treatments may be treatments that the user may have previously picked up via a pharmacy selected at step 114 of the flowchart 100 of FIG. 1. The list of treatments may be stored locally at the user device or may be stored at a remote location accessible by cloud electronic system 210. The user may access the list of treatments by using a user device to access a platform (e.g., an application or other software) that is associated with cloud electronic system 210. Accordingly, at step 802 of FIG. 800, a user may select a treatment from a list of previously provided treatments. According to an implementation, the list of treatments may be limited to those treatments that are available for the user. For example, the list of treatments may exclude any treatments that require a refill and for which no refill is available.

At step 804, a plurality of updated pharmacies may be identified based on availability of the treatment and a location criterion. Step 804 of FIG. 8 is similar to step 108 of FIG. 1 and, for brevity, the disclosure related to step 108 of FIG. 1 is not repeated herein. However, at step 804, the plurality of updated pharmacies may be identified at a time subsequent to the step 108 of FIG. 1. Further, it will be understood that the available pharmacies and/or the location criterion may be different than the available pharmacies and/or the location criterion applied at step 108 of FIG. 1. As an example, the difference may simply be based on a duration of time such that, given the duration of time, the available pharmacies may change and/or the user's current and/or preferred location may change.

At step 806 of FIG. 8, treatment pricing information of the treatment for each of the updated pharmacies may be obtained in a manner similar to step 110 of FIG. 1. At step 808, the plurality of updated pharmacies and the corresponding pricing information may be transmitted in a manner similar to step 112 of FIG. 1. At step 810, a selection of an updated pharmacy may be received in a manner similar to step 114 of FIG. 1. At step 812, a prescription associated with the treatment selected at step 802 may be transmitted to the updated pharmacy selected at step 810, in a manner similar to step 116. For brevity, the disclosure related to steps 110, 112, 114, and 116 of FIG. 1 is not repeated herein. It will be understood that one or more steps of flowchart 800 may be performed simultaneously or in an order different than that shown in FIG. 8. The order shown in FIG. 8 is for convenience only and is not meant to show the only order that the techniques disclosed herein can be performed.

According to implementations, a treatment may be a procedure (e.g., medical procedure, body sample test, physical therapy procedure, osteopathic medicine procedure, etc.). For example, a user may have a referral or request for an outpatient medical treatment that needs to be fulfilled, for example, x-rays, medical scans, medical tests, etc. Notably, the price of such a procedure based treatment may vary from office to office (i.e., pharmacy to pharmacy as applied herein). The set of prices may be for outpatient treatments and the information input from the user may include desired locations, office hours, treatment types, etc. Based on this data, the system may generate a list based on outpatient medical offices within the user's desired location in a manner similar to that described in FIGS. 1 and 8. As described in FIGS. 1 and 8, once the list is transmitted to the user, the user may select an outpatient medical office, such that the referral or medical order is transmitted to the selected outpatient medical office, and the user can make an appointment. The user may also make their appointments with the medical offices through the system.

According to implementations of the present disclosure, data and information from users other than a registered user may be collected and aggregated. Such information may be anonymized or otherwise transformed to comply with patient privacy requirements such as those applied via applicable HIPPA requirements. For example, such information may include the frequency of refills based on locations and/or demographics, and the duration between refills and new prescriptions. This data may be beneficial for third-parties, such as pharmaceutical companies, healthcare companies, and pharmacy benefit managers. For example, third-parties may receive trending data if a large number of prescriptions for a certain treatment are being fulfilled at a certain pharmacy or pharmacies within a designated location. This data may show if a pharmacy's supply is going to be limited or needs to be stocked. Data may also show if certain drugs are refilled a minimal amount of times before users try a different prescription drug, such as a different brand name, generic version, or alternative therapy.

The collected data may also be presented to a given user when the user is selecting a pharmacy. For example, trending data may show if a certain number of users from a specified insurance company are fulfilling their prescriptions for the same drug at the same pharmacy. This may be a result of, for example, low prices or availability of the prescribed drug. Once this data is presented to the user (e.g., in addition to the map 600 of FIG. 6), that user may apply the data as a factor when selecting a pharmacy. Such aggregated data may also show if a certain threshold of users under the same insurance plan switch from one pharmacy to a more popular pharmacy. This information may be useful to a user, because the data may show that the more popular pharmacy may have overall better prices, better customer service, increased availability of prescription drugs, less wait times, etc.

The disclosed systems (e.g., cloud electronic system 210) may communicate with third-party platforms, for example, review platforms, such as Yelp® or Consumer Reports®. Reviews may be pulled from these platforms and associated with the list transmitted to the user, so that the user may see their inputted data, drug pricing, and reviews from other users. For example, the reviews may discuss a pharmacy's customer service/convenience/operations, such that the user can select a pharmacy with great pricing, as well as one that is highly rated among other users and users.

As disclosed herein, the platform may be a user application on a mobile device, the mobile device being capable of determining its location based on data obtained by a component (e.g., GPS chip, software, or firmware) included in the mobile device. In an example implementation, the system may provide a notification based on a location of the mobile device. For example, if a user is near a pharmacy, whether or not the user has selected that pharmacy to fulfill a prescription, the system may notify the user of the pharmacy's wait times, operating hours, availability of any prescription drugs within the user's queue, etc. This implementation may be especially useful for users who have moved or who are traveling.

According to an implementation, businesses and companies may provide insurance coverage to their employees based on the techniques and systems disclosed herein. Such businesses may encourage their employees to use the discussed platform (e.g., application, software, etc.). In addition to the disclosed capabilities, the platform may receive information on the specific coverage, so that when the employees (i.e., users) use the application, the lists will include how much the prescribed drug or medical treatment is actually costing the business. In at least one example, a list of pharmacies may be transmitted to the user comparing the price for the drug or medical treatment under the insurance plan compared to what it would cost without an insurance plan. The employees can then make an educated decision on how to pay for the medication or treatment.

Unless specifically stated otherwise, as apparent from the following discussions, it is appreciated that throughout the specification discussions utilizing terms such as "processing," "computing," "calculating," "determining", "analyzing" or the like, refer to the action and/or processes of a computer or computing system, or similar electronic computing device, that manipulate and/or transform data represented as physical, such as electronic, quantities into other data similarly represented as physical quantities.

In a similar manner, the term "processor" may refer to any device or portion of a device that processes electronic data, e.g., from registers and/or memory to transform that electronic data into other electronic data that, e.g., may be stored in registers and/or memory. An "electronic device", a "cloud electronic device", a "computer," a "computing machine," a "computing platform," a "computing device," or a "server" may include one or more processors.

Figure 9:
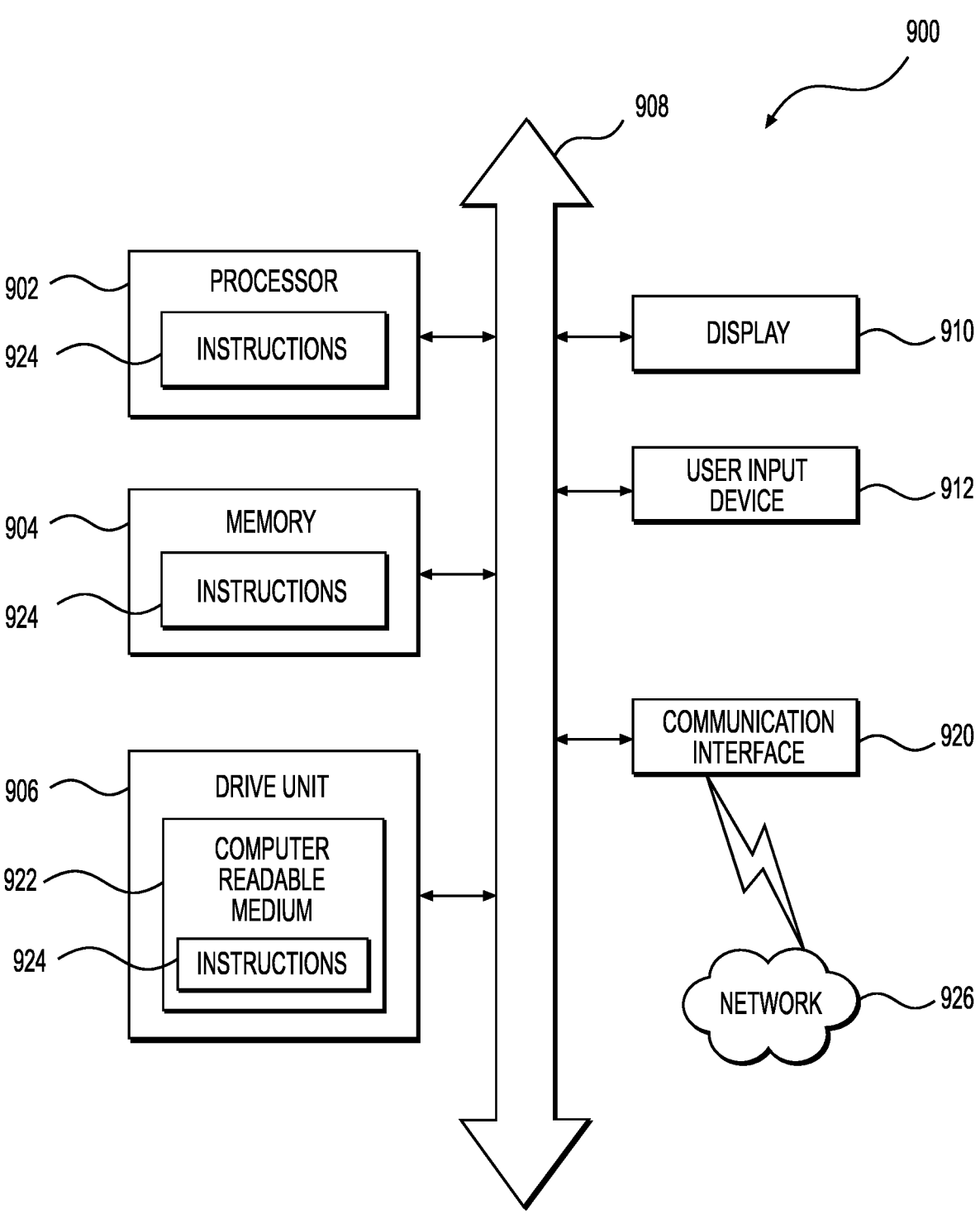
FIG. 9 shows an exemplary implementation of a computer system, according to an embodiment of the present disclosure.

FIG. 9 illustrates an implementation of an electronic system 900 that may execute techniques presented herein. For example, some or all of the electronic system 900 may be part of or may be mobile device 202, laptop 204, desktop 206, server 208, cloud electronic system 210, internet portal 214, a prescription submission system, a pharmacy identification system, a pricing analysis system, a location analysis system, a prescription processing system, or the like. The electronic system 900 can include a set of instructions that can be executed to cause the electronic system 900 to perform any one or more of the methods or computer based functions disclosed herein. The electronic system 900 may operate as a standalone device or may be connected, e.g., using a network, to other electronic systems or peripheral devices, as shown in FIG. 2.

In a networked deployment, the electronic system 900 may operate in the capacity of a server or as a client user computer in a server-client user network environment, or as a peer electronic system in a peer-to-peer (or distributed) network environment. The electronic system 900 can also be implemented as or incorporated into various devices, such as a personal computer (PC) (e.g., desktop 206), a tablet PC, a set-top box (STB), a personal digital assistant (PDA), a mobile device (e.g., mobile device 202), a palmtop computer, a laptop computer (e.g., laptop 204), a desktop computer (e.g., desktop 206), a communications device (e.g., mobile device 202), a wireless telephone (e.g., mobile device 202), a land-line telephone, a control system, a camera, a scanner, a facsimile machine, a printer, a pager, a personal trusted device, a web appliance, a network router, switch or bridge, or any other machine capable of executing a set of instructions (sequential or otherwise) that specify actions to be taken by that machine. In a particular implementation, the electronic system 900 can be implemented using electronic devices that provide voice, video, or data communication. Further, while a single electronic system 900 is illustrated, the term "system" shall also be taken to include any collection of systems or sub-systems that individually or jointly execute a set, or multiple sets, of instructions to perform one or more computer functions.

As illustrated in FIG. 9, the electronic system 900 may include a processor 902, e.g., a central processing unit (CPU), a graphics processing unit (GPU), or both. Processor 902 may be a component in a variety of systems. For example, processor 902 may be part of a standard personal computer or a workstation. Processor 902 may be one or more general processors, digital signal processors, application specific integrated circuits, field programmable gate arrays, servers, networks, digital circuits, analog circuits, combinations thereof, or other now known or later developed devices for analyzing and processing data. The processor 902 may implement a software program, such as code generated manually (i.e., programmed).

The electronic system 900 may include a memory 904 that can communicate via a bus 908. Memory 904 may be a main memory, a static memory, or a dynamic memory. Memory 904 may include, but is not limited to computer readable storage media such as various types of volatile and non-volatile storage media, including but not limited to random access memory, read-only memory, programmable read-only memory, electrically programmable read-only memory, electrically erasable read-only memory, flash memory, magnetic tape or disk, optical media and the like. In one implementation, memory 904 includes a cache or random-access memory for processor 902. In alternative implementations, memory 904 is separate from processor 902, such as a cache memory of a processor, the system memory, or other memory. Memory 904 may be an external storage device or database for storing data. Examples include a hard drive, compact disc ("CD"), digital video disc ("DVD"), memory card, memory stick, floppy disc, universal serial bus ("USB") memory device, or any other device operative to store data. The memory 904 is operable to store instructions executable by processor 902. The functions, acts, or tasks illustrated in the figures or described herein may be performed by processor 902 executing the instructions stored in memory 904. The functions, acts, or tasks are independent of the particular type of instructions set, storage media, processor, or processing strategy and may be performed by software, hardware, integrated circuits, firmware, micro-code, and the like, operating alone or in combination. Likewise, processing strategies may include multiprocessing, multitasking, parallel processing, and the like.

As shown, electronic system 900 may further include a display 910, such as a liquid crystal display (LCD), an organic light emitting diode (OLED), a flat panel display, a solid-state display, a cathode ray tube (CRT), a projector, a printer, or other now known or later developed display device for outputting determined information. Display 910 may act as an interface for the user to see the functioning of processor 902, or specifically as an interface with the software stored in memory 904 or in drive unit 906.

Additionally or alternatively, the electronic system 900 may include an input device 912 configured to allow a user to interact with any of the components of system 900. Input device 912 may be a number pad, a microphone, a sensor, a keyboard, or a cursor control device, such as a mouse, or a joystick, touch screen display, remote control, or any other device operative to interact with the electronic system 900.

Electronic system 900 may also or alternatively include a disk or optical drive unit 906. Disk or optical drive unit 906 may include a computer-readable medium 922 in which one or more sets of instructions 924, e.g. software, can be embedded. Further, instructions 924 may embody one or more of the methods or logic as described herein. Instructions 924 may reside completely or partially within memory 904 and/or within processor 902 during execution by electronic system 900. Memory 904 and processor 902 also may include computer-readable media as discussed above.

In some systems, a computer-readable medium 922 includes instructions 924 or receives and executes instructions 924 responsive to a propagated signal so that a device connected to a network 926 can communicate voice, video, audio, images, or any other data over network 926. For example, network 926 may be similar to or the same as internet portal 214 of FIG. 2. Further, instructions 924 may be transmitted or received over network 926 via a communication port or interface 920, and/or using a bus 908. Communication port or interface 920 may be a part of processor 902 or may be a separate component. Communication port or interface 920 may be created in software or may be a physical connection in hardware. Communication port or interface 920 may be configured to connect with network 926, external media, display 910, or any other components in system 900, or combinations thereof. The connection with network 926 may be a physical connection, such as a wired Ethernet connection or may be established wirelessly as discussed below. Likewise, the additional connections with other components of the system 900 may be physical connections or may be established wirelessly. Network 926 may alternatively be directly connected to the bus 908.

While the computer-readable medium 922 is shown to be a single medium, the term "computer-readable medium" may include a single medium or multiple media, such as a centralized or distributed database, and/or associated caches and servers that store one or more sets of instructions. The term "computer-readable medium" may also include any medium that is capable of storing, encoding, or carrying a set of instructions for execution by a processor or that cause an electronic system to perform any one or more of the methods or operations disclosed herein. Computer-readable medium 922 may be non-transitory, and may be tangible.

Computer-readable medium 922 can include a solid-state memory such as a memory card or other package that houses one or more non-volatile read-only memories. Computer-readable medium 922 can be a random-access memory or other volatile re-writable memory. Additionally or alternatively, computer-readable medium 922 can include a magneto-optical or optical medium, such as a disk or tapes or other storage device to capture carrier wave signals such as a signal communicated over a transmission medium. A digital file attachment to an e-mail or other self-contained information archive or set of archives may be considered a distribution medium that is a tangible storage medium. Accordingly, the disclosure is considered to include any one or more of a computer-readable medium or a distribution medium and other equivalents and successor media, in which data or instructions may be stored.

In an alternative implementation, dedicated hardware implementations, such as application specific integrated circuits, programmable logic arrays and other hardware devices, can be constructed to implement one or more of the methods described herein. Applications that may include the apparatus and systems of various implementations can broadly include a variety of electronic and electronic systems. One or more implementations described herein may implement functions using two or more specific interconnected hardware modules or devices with related control and data signals that can be communicated between and through the modules, or as portions of an application-specific integrated circuit. Accordingly, the present system encompasses software, firmware, and hardware implementations.

Electronic system 900 may be connected to one or more networks 926 (e.g., internet portal 214 of FIG. 2). Network 926 may define one or more networks including wired or wireless networks. The wireless network may be a cellular telephone network, an 802.11, 802.16, 802.20, or WiMax network. Further, such networks may include a public network, such as the Internet, a private network, such as an intranet, or combinations thereof, and may utilize a variety of networking protocols now available or later developed including, but not limited to TCP/IP based networking protocols. The network 926 may include wide area networks (WAN), such as the Internet, local area networks (LAN), campus area networks, metropolitan area networks, a direct connection such as through a Universal Serial Bus (USB) port, or any other networks that may allow for data communication. Network 926 may be configured to couple one computing device to another computing device to enable communication of data between the devices. Network 926 may generally be enabled to employ any form of machine-readable media for communicating information from one device to another. Network 926 may include communication methods by which information may travel between computing devices. Network 926 may be divided into sub-networks. The sub-networks may allow access to all of the other components connected thereto or the sub-networks may restrict access between the components. Network 926 may be regarded as a public or private network connection and may include, for example, a virtual private network or an encryption or other security mechanism employed over the public Internet, or the like.

In accordance with various implementations of the present disclosure, the methods described herein may be implemented by software programs executable by an electronic system. Further, in an exemplary, non-limited implementation, implementations can include distributed processing, component/object distributed processing, and parallel processing. Alternatively, virtual electronic system processing can be constructed to implement one or more of the methods or functionality as described herein.

Although the present specification describes components and functions that may be implemented in particular implementations with reference to particular standards and protocols, the disclosure is not limited to such standards and protocols. For example, standards for Internet and other packet switched network transmission (e.g., TCP/IP, UDP/IP, HTML, HTTP) represent examples of the state of the art. Such standards are periodically superseded by faster or more efficient equivalents having essentially the same functions. Accordingly, replacement standards and protocols having the same or similar functions as those disclosed herein are considered equivalents thereof.

It will be understood that the steps of methods discussed are performed in one embodiment by an appropriate processor (or processors) of a processing (i.e., computer) system executing instructions (computer-readable code) stored in storage. It will also be understood that the invention is not limited to any particular implementation or programming technique and that the invention may be implemented using any appropriate techniques for implementing the functionality described herein. The invention is not limited to any particular programming language or operating system.

It should be appreciated that in the above description of exemplary embodiments of the invention, various features of the invention are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that the claimed invention requires more features than are expressly recited in each claim. Rather, as the following claims reflect, inventive aspects lie in less than all features of a single foregoing disclosed embodiment. Thus, the claims following the Detailed Description are hereby expressly incorporated into this Detailed Description, with each claim standing on its own as a separate embodiment of this invention.

Furthermore, while some embodiments described herein include some but not other features included in other embodiments, combinations of features of different embodiments are meant to be within the scope of the invention, and form different embodiments, as would be understood by those skilled in the art. For example, in the following claims, any of the claimed embodiments can be used in any combination.

Furthermore, some of the embodiments are described herein as a method or combination of elements of a method that can be implemented by a processor of an electronic system or by other means of carrying out the function. Thus, a processor with the necessary instructions for carrying out such a method or element of a method forms a means for carrying out the method or element of a method. Furthermore, an element described herein of an apparatus embodiment is an example of a means for carrying out the function performed by the element for the purpose of carrying out the invention.

In the description provided herein, numerous specific details are set forth. However, it is understood that embodiments of the invention may be practiced without these specific details. In other instances, well-known methods, structures and techniques have not been shown in detail in order not to obscure an understanding of this description.

Similarly, it is to be noticed that the term coupled, when used in the claims, should not be interpreted as being limited to direct connections only. The terms "coupled" and "connected," along with their derivatives, may be used. It should be understood that these terms are not intended as synonyms for each other. Thus, the scope of the expression a device A coupled to a device B should not be limited to devices or systems wherein an output of device A is directly connected to an input of device B. It means that there exists a path between an output of A and an input of B which may be a path including other devices or means. "Coupled" may mean that two or more elements are either in direct physical or electrical contact, or that two or more elements are not in direct contact with each other but yet still co-operate or interact with each other.

Thus, while there has been described what are believed to be the preferred embodiments of the invention, those skilled in the art will recognize that other and further modifications may be made thereto without departing from the spirit of the invention, and it is intended to claim all such changes and modifications as falling within the scope of the invention. For example, any formulas given above are merely representative of procedures that may be used. Functionality may be added or deleted from the block diagrams and operations may be interchanged among functional blocks. Steps may be added or deleted to methods described within the scope of the present invention.

The above disclosed subject matter is to be considered illustrative, and not restrictive, and the appended claims are intended to cover all such modifications, enhancements, and other implementations, which fall within the true spirit and scope of the present disclosure. Thus, to the maximum extent allowed by law, the scope of the present disclosure is to be determined by the broadest permissible interpretation of the following claims and their equivalents, and shall not be restricted or limited by the foregoing detailed description. While various implementations of the disclosure have been described, it will be apparent to those of ordinary skill in the art that many more implementations and implementations are possible within the scope of the disclosure. Accordingly, the disclosure is not to be restricted except in light of the attached claims and their equivalents.

What is claimed is:

1. A computer-implemented method for prescription management, the method comprising:

receiving, from a user computing device of a user, user information of the user, a location associated with the user, and a prescription at one or more processors of a cloud electronic system, wherein the prescription is associated with the user information, includes a treatment, and is received in a first format, providing, by the cloud electronic system, the user information, the location, and the treatment as inputs to a trained machine learning model, wherein the trained machine learning model is trained using supervised learning based on training data including one or more of pharmacy-specific historical data and historical user pharmacy selection data;

receiving, at the cloud electronic system, from the trained machine learning model, a machine learning model output comprising identified pharmacies filtered from a plurality of pharmacies, based on the user information, the location, and the treatment being applied to each identified pharmacy of the plurality of pharmacies;

identifying, at the cloud electronic system, treatment pricing information for each of identified pharmacies;

determining, at the cloud electronic system, an order of the identified pharmacies based on the treatment pricing information for each of the identified pharmacies;

providing, by the cloud electronic system, the identified pharmacies ordered based on the order of pharmacies to the user computing device;

receiving, at the cloud electronic system, a selected pharmacy from the pharmacies;

modifying, at the cloud electronic system, the prescription in the first format to a second format, wherein the second format is selected based on the selected pharmacy; and transmitting, via the cloud electronic system, the prescription in the second format to a pharmacy prescription processing system of the selected pharmacy.

2. The method of claim 1, further comprising:

receiving, at the cloud electronic system, an updated pharmacy;

generating, at the cloud electronic system, an updated formatted prescription for the treatment having a third format accepted by a second prescription processing system of the updated pharmacy and corresponding to the prescription being received in the first format; and transmitting, via the cloud electronic system, the updated formatted prescription to the second pharmacy processing system.

3. The method of claim 1, wherein the user information comprises at least one of insurance information, time preference information, discount information, rewards information, or review preference information.

4. The method of claim 1, further comprising:

determining, at the cloud electronic system, one or more alternative treatments corresponding to the treatment; and identifying, at the cloud electronic system, the pharmacies based on the one or more alternative treatments.

5. The method of claim 1, wherein identifying pricing information comprises adjusting a base treatment pricing based on the user information.

6. The method of claim 1, wherein identifying treatment pricing information comprises adjusting a base treatment pricing based on insurance information.

7. The method of claim 1, wherein the prescription in the first format is provided by a health care provider system.

8. The method of claim 1, wherein the pharmacies are filtered based on a location criterion selected from at least one of a distance proximity, a time proximity, a minimum number of pharmacies, or a combination thereof.

9. The method of claim 1, wherein the treatment is one of a medicine, a therapy, a device, an application, an object, or combinations thereof.

10. The method of claim 1, further comprising:

accessing, via an Application Programing Interface (API), fulfillment information for one or more other users for the treatment based on prescriptions for the treatment fulfilled at each of the pharmacies, the fulfilment information being anonymized relative to the one or more other users;

determining, at the cloud electronic system, trending data based on the fulfillment information relative to at least one of:

inventory information including inventory of the treatment at each of the filtered plurality of pharmacies, or insurance information associated with the one or more other users; and generating, at the cloud electronic system, a graphic user interface (GUI) to include the trending data, wherein the trending data is ordered based on the at least one of the inventory information and the insurance information.

11. The method of claim 1, wherein the user computing device is a mobile device.

12. The method of claim 1, further comprising transmitting, via the cloud electronic system, the pharmacies and respective treatment pricing information in a format that visually shows the pharmacies and the treatment pricing information on a map.

13. A computer-implemented method for prescription management, the method comprising:

accessing one or more prescriptions stored on a user device, wherein the one or more prescriptions are stored in a first format;

selecting a first prescription from the one or more prescriptions, the first prescription comprising a first treatment;

receiving a location from the user device;

providing the location and the first treatment as an input to a first trained machine learning model, wherein the first trained machine learning model is trained using supervised learning based on training data including one or more of pharmacy specific historical data, treatment historical data, and historical user pharmacy selection data to output one or more pharmacies;

receiving, from the first trained machine learning model, a first machine learning output comprising identified pharmacies filtered from a plurality of pharmacies, wherein the plurality of pharmacies are filtered based on a likelihood of availability of the first treatment at each of the plurality of pharmacies that meet a location criterion based on the location;

identifying treatment pricing information for each of the identified pharmacies;

providing the location and the treatment pricing information for each of the identified pharmacies to a second trained machine learning model, wherein the second trained machine learning model is trained using supervised learning based on training data including one or more of pharmacy-specific historical data and historical user pharmacy selection data;

receiving, from the second trained machine learning model, a selected pharmacy from the identified pharmacies;

modifying the first prescription in the first format to a second format, wherein the second format is selected based on the selected pharmacy; and transmitting the prescription to a prescription processing system of the selected pharmacy.

14. The method of claim 13, further comprising:

determining one or more alternative treatments corresponding to the first treatment; and identifying the pharmacies based on the one or more alternative treatments.

15. The method of claim 13, wherein the location criterion is selected from at least one of a distance proximity, a time proximity, a minimum number of pharmacies, or a combination thereof.

16. The method of claim 13, wherein the first treatment is a previous treatment picked up by the user.

17. A system comprising:

a user computing device, comprising at least one processor;

a cloud electronic system, comprising at least one processor;

the user computing device configured to allow a user to:

access one or more prescriptions stored on the user computing device, wherein the one or more prescription are stored in a first format, and select a first prescription from the one or more prescriptions, the first prescription comprising a first treatment;

the cloud electronic system configured to:

receive a location from the user computing device;

receive the first treatment from the user computing device;

provide the location and the first treatment as inputs to a first trained machine learning model, wherein the first trained machine learning model is trained using supervised learning based on training data including one or more of pharmacy-specific historical data and historical user pharmacy selection data to output one or more pharmacies;

receive, from the first trained machine learning model, a first machine learning model output comprising identified pharmacies filtered from a plurality of pharmacies, wherein the plurality of pharmacies are filtered based on a likelihood of availability of the first treatment at each of the plurality of pharmacies that meet a location criterion based on the location;

identify treatment pricing information for each of the identified pharmacies;

provide the location and the treatment pricing information for each of the identified pharmacies to a second trained machine learning model, wherein the second trained machine learning model is trained using supervised learning based on training data including one or more of pharmacy-specific historical data and historical user pharmacy selection data;

receive, from the second trained machine learning model, a selected pharmacy from the identified pharmacies;

modify the first prescription in the first format to a second format, wherein the second format is selected based on the selected pharmacy; and transmit the prescription to a prescription processing system of the selected pharmacy.

18. The system of claim 17, wherein the first treatment is a previous treatment picked up by the user.

19. The system of claim 17, wherein the user computing device is at least one of a mobile phone, a laptop, or a desktop.

20. The system of claim 17, wherein the cloud electronic system is further configured to:

determine one or more alternative treatments corresponding to the first treatment; and identify the pharmacies based on the one or more alternative treatments.

* * * * *